(12) United States Patent
Berthel et al.

(10) Patent No.: US 7,803,816 B2
(45) Date of Patent: Sep. 28, 2010

(54) MCH RECEPTOR ANTAGONISTS

(75) Inventors: Steven Joseph Berthel, Mendham Township, NJ (US); Shawn David Erickson, Leonia, NJ (US); Nader Fotouhi, Basking Ridge, NJ (US); Robert Francis Kester, West Orange, NJ (US); Kyungjin Kim, Livingston, NJ (US); Steven Gregory Mischke, Florham Park, NJ (US); Yimin Qian, Wayne, NJ (US); Kshitij Chhabilbhai Thakkar, Clifton, NJ (US); Jefferson Wright Tilley, North Caldwell, NJ (US); Hong Wang, Nutley, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 953 days.

(21) Appl. No.: 11/526,523

(22) Filed: Sep. 25, 2006

(65) Prior Publication Data

US 2007/0078165 A1    Apr. 5, 2007

Related U.S. Application Data

(60) Provisional application No. 60/722,610, filed on Sep. 30, 2005.

(51) Int. Cl.
*A61K 31/454* (2006.01)
*C07D 403/02* (2006.01)

(52) U.S. Cl. ........................................ 514/322; 546/199
(58) Field of Classification Search ................. 514/322; 546/199
See application file for complete search history.

(56) References Cited

U.S. PATENT DOCUMENTS

| 6,258,825 | B1 * | 7/2001 | Ozaki et al. .............. 514/322 |
| 7,495,109 | B2 * | 2/2009 | Sun et al. ................ 548/304.4 |
| 2005/0040257 | A1 | 2/2005 | Seitz |
| 2005/0075355 | A1 | 4/2005 | Den Hartog et al. |
| 2005/0137243 | A1 | 6/2005 | Souers et al. |

FOREIGN PATENT DOCUMENTS

| EP | 0 990 653 A1 | 4/2000 |
| EP | 1 069 124 A1 | 1/2001 |
| WO | WO01/21577 | 3/2001 |
| WO | WO02/051809 | 7/2002 |
| WO | WO02/089729 | 11/2002 |
| WO | WO03/045313 | 6/2003 |
| WO | WO 03/088967 A1 | 10/2003 |
| WO | WO03/105850 | 12/2003 |
| WO | WO2004/072025 | 8/2004 |
| WO | WO2004092181 | 10/2004 |
| WO | WO2005/019167 | 3/2005 |
| WO | WO2005/019240 | 3/2005 |
| WO | WO 2005/021528 A1 | 3/2005 |
| WO | WO2005/034947 | 4/2005 |
| WO | WO2005/042541 | 5/2005 |

OTHER PUBLICATIONS

Moss et al. "A new class . . . " CA151:501 (2009).*
Sheppard et al. "Indole-3-carbonyl . . . " CA 125:328713 (1996).*
Kawauchi, Nature 305, 321-333, (1983).
Qu, et. al. (1996) Nature, 380: 243-247.
Rossi, et. al. (1997) Endocrinology 138: 351-355.
Shimada, et. al. (1998) Nature 396: 670-674.
Borowsky, et. al. (2002) Nature Medicine 8(8): 825-830.
Souers, et. al. (2005) Bioorg Med Chem 15: 2752-2757.
Vasudevan, et. al. (2005) Bioorg Med Chem 15: 4174-4179.
Kym, et. al. (2005) J Med Chem 5888-91.
McBriar (2005) J Med Chem 48: 2274.
Takekawa (2002) Eur J Pharm 438(3): 129-135.
Kowalski, Eur J Pharm (2004) 497: 41-47.
Hervieu (2003) Expert Opin on Thera Targets 7(4) 495-511.
Georgescu (2005) Jour of Neuro 25(11), 2933-2940.
Chaki (2005) Jour of Pharm 313, 831-839.
Adamantidis (2005) Eur Jour of Neuroscience 21, 2837-2844.

* cited by examiner

*Primary Examiner*—Celia Chang
(74) *Attorney, Agent, or Firm*—George W. Johnston; Dennis P. Tramaloni; Samuel H. Megerditchian

(57) ABSTRACT

Provided herein are compounds of the formula (I):

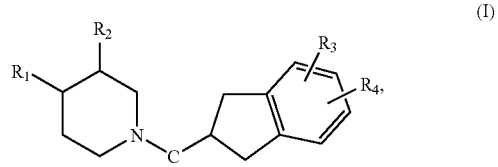

as well as pharmaceutically acceptable salts thereof, wherein the substituents are as those disclosed in the specification. These compounds, and the pharmaceutical compositions containing them, are useful for the treatment of obesity, hyperphagia, anxiety, depression and related disorders and diseases.

16 Claims, No Drawings

MCH RECEPTOR ANTAGONISTS

PRIORITY TO RELATED APPLICATIONS

This application claims the benefit of U.S. Provisional Application No. 60/722,610, filed Sep. 30, 2005, which is hereby incorporated by reference in its entirety.

FIELD OF THE INVENTION

The invention relates to melanin-concentrating hormone receptor antagonists and derivatives thereof. The antagonists and derivatives thereof are useful for the treatment of obesity, hyperphagia, anxiety, depression and related disorders and diseases.

All documents cited or relied upon below are expressly incorporated herein by reference.

BACKGROUND OF THE INVENTION

Melanin-concentrating hormone (MCH) is a cyclic peptide that was first isolated from the pituitary of chum salmon (Kawauchi, Nature 305, 321-333). The sequence for MCH has been shown to be identical in all teleost fish where it causes melanin granulation and, hence, regulates color change. Recent reports also suggest MCH plays a role in food intake in teleosts. MCH also inhibits release of ACTH thus acting as an antagonist of α-MSH. MCH was subsequently identified in mammals as a cyclic nonapeptide. The first MCH receptor (later termed MCHR1) is a G-protein coupled receptor (GPCR) and was identified using a "reverse pharmacology" approach. That is, it was demonstrated that the natural ligand of orphan GPCR, SLC-1, was MCH in mammals. Subsequent to this determination, a second MCH receptor (MCHR-2) has been identified. The role of MCH in feeding behavior in mammals has been the subject of investigation for a number of years (Qu, et al. (1996) *Nature*, 380: 243-247; Rossi et al. (1997) *Endocrinology* 138: 351-355; Shimada et al. (1998) *Nature* 396: 670-674). MCH is predominantly expressed in the lateral hypothalamus and the zona incerta of the central nervous system (CNS). Central administration of MCH is known to stimulate food intake and regulate energy balance. MCH is upregulated in the lateral hypothalamus during fasting (Rossi et al. (1997) *Endocrinology* 138: 351-355). Knockout experiments have shown that mice lacking the MCH peptide are lean, hypophagic and maintained elevated metabolic rates. MCH mRNA levels are increased in both normal and obese mice. Transgenic mice that overexpress MCH are obese and insulin resistant. Genetically altered animals that lack the gene encoding the MCH receptor are moderately hyperphagic but show resistance to becoming obese and have an increased metabolic rate (Shimada et al. (1998) *Nature* 396: 670-674). MCH is thought to exert its effects on feeding behavior by binding to an MCH receptor (MCHR1 or MCHR2) resulting in mobilization of intracellular calcium and a concomitant reduction in cyclic AMP levels. The consistency in these findings suggests that MCH antagonism could safely lead to weight loss in humans. In further support of this, a number of studies describe statistically significant reduction of food intake in rodents following acute administration of MCH receptor antagonists and/or statistically significant reduction of body weight after chronic administration of small molecule MCH receptor antagonists (Borowsky et al. (2002) *Nature Medicine* 8(8):825-830; Souers et al. (2005) *Bioorg. Med. Chem. Lett.* 15: 2752-2757; Vasudevan et al. (2005) *Bioorg. Med. Chem. Lett.* 15: 4174-4179, Kym et al. (2005) *J. Med. Chem.* 5888-91; McBriar et al. (2005) *J. Med. Chem.* 48: 2274); Takekawa et al. (2002) *Eur. J. Pharmacol.* 438(3): 129-135; Kowalski et al. *Eur. J. Pharmacol.* (2004) 497: 41-47). The precise role of MCH in attenuating food intake is not clear from these studies because the small-molecule MCH receptor antagonists described are either 1) unselective for the MCH receptor or 2) no selectivity data is disclosed.

MCHR1 antagonism with a small molecule is now recognized as a promising strategy for the treatment of obesity. The following relate to small-molecule MCH receptor antagonists: Kato et al. WO2001/21577; Chen et al. WO2002/089729; Collins et al. WO2003/105850; Souers et al. US2005/0137243; Hulme et al. WO2005/019167; Tempest et al. WO2005/019240; Barvian et al. WO2004092181; Barvian et al. WO2005/042541; McKittrick et al. WO2002/051809; Sasikumar et al. WO2005/034947; Devita et al. WO2003/045313; Gillig et al. 2005/040257; and Schwink et al. WO2004/072025.

MCH has been shown to modulate behaviors and disease states other than hyperphagia and obesity. MCHR1 antagonists have been shown to inhibit behavior in rodents that models depression and anxiety in humans (Hervieu (2003) *Expert Opinion on Therapeutic Targets* 7(4), 495-511 and references therein; Georgescu et al. (2005) *Journal of Neuroscience* 25(11), 2933-2940; Chaki et al. (2005) *Journal of Pharm. and Exptl. Therapeutics* 313, 831-839). These rodent models include forced swim test, vocalization and various models of social interaction. Recent studies also support a role of MCHR1 in cognition (Adamantidis et al. (2005) *European Journal of Neuroscience* 21, 2837-2844).

There is still a need for selective MCH receptor antagonists in order to address the role of the MCH receptor in food intake and regulation of body weight. Unlike a number of existing medications for weight loss, it is believed that a selective MCH receptor antagonist would provide a means of safely reducing food intake and body weight in humans. Such selective MCH receptor antagonists would be useful for the treatment of, for example, obesity, hyperphagia, anxiety, depression and related disorders.

SUMMARY OF THE INVENTION

In one embodiment of the present invention, provided is a compound of the formula (I):

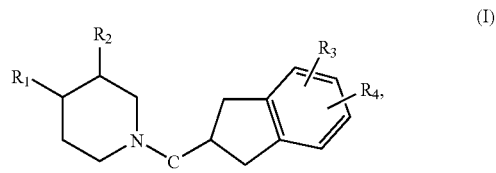

wherein:

$R_1$ is benzimidazole or azabenzimidazole, unsubstituted or mono-, bi- or tri-substituted with a group selected from the group consisting of halogen, hydroxyl, —SCH$_3$, phenyl, ($C_3$-$C_6$)cycloalkyl, oxygen, ($C_1$-$C_6$)alkoxy, branched or unbranched ($C_1$-$C_6$)alkyl and branched or unbranched ($C_1$-$C_6$)alkyl substituted with hydroxyl;

$R_2$ is hydrogen, halogen, substituted or unsubstituted ($C_1$-$C_6$) alkyl, hydroxyl, —OCH$_2$C(CH$_3$)OH, —SCH$_3$, —OSO$_2$CH$_3$, ($C_1$-$C_6$)alkoxy, —CH$_2$OH or —CH$_2$OCH$_3$;

$R_3$ is H or halogen;

$R_4$ is hydrogen, halogen, $(C_1-C_6)$alkyl, —CN, —NH$_2$, —NHCH$_3$, —NHCO—$R_5$, —OCH$_3$ or azaindane;

$R_5$ is substituted or unsubstituted, branched or unbranched $(C_1-C_6)$alkyl, $(C_1-C_6)$alkoxy; $(C_3-C_6)$cycloalkyl, unsubstituted saturated, unsaturated or partially saturated heterocycle which is a 5- or 6-membered heteroaromatic ring connected by a ring carbon which has from 1 to 3 hetero ring atoms selected from the group consisting of S, N and O;

and pharmaceutically acceptable salts thereof.

In another embodiment of the present invention, provided is a pharmaceutical composition comprising a therapeutically effective amount of a compound according to formula (I) or a pharmaceutically acceptable salt thereof, and a pharmaceutically acceptable carrier.

In a further embodiment of the present invention, provided is method for treating obesity in a patient in need of such treatment, comprising administering a therapeutically effective amount of a compound according to formula (I) or a pharmaceutically acceptable salt thereof to a patient in need thereof.

DETAILED DESCRIPTION OF THE INVENTION

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl" means, for example, a branched or unbranched, cyclic or acyclic, saturated or unsaturated (e.g. alkenyl or alkynyl) hydrocarbyl radical which may be substituted or unsubstituted. Where cyclic, the alkyl group is preferably $C_3$ to $C_{12}$, more preferably $C_4$ to $C_{10}$, more preferably $C_4$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

As used herein, the term "lower alkyl" means, for example, a branched or unbranched, cyclic or acyclic, saturated or unsaturated (e.g. alkenyl or alkynyl) hydrocarbyl radical wherein said cyclic lower alkyl group is $C_5$, $C_6$ or $C_7$, and wherein said acyclic lower alkyl group is $C_1$, $C_2$, $C_3$, $C_4$, $C_5$, or $C_6$, preferably from 1 to 4 carbon atoms. Typical lower alkyl groups include methyl, ethyl, propyl (n-propyl or isopropyl), butyl (n-butyl, isobutyl or tertiary-butyl), pentyl and hexyl. It will be appreciated therefore that the term "lower alkyl" as used herein includes, for example, lower alkyl (branched or unbranched), lower alkenyl (branched or unbranched), lower alkynyl (branched or unbranched), cycloloweralkyl, cycloloweralkenyl and cycloloweralkynyl. When attached to another functional group, lower alkyl as used herein may be divalent, e.g., -lower alkyl-COOH.

As used herein, the term "aryl" means, for example, a substituted or unsubstituted carbocyclic aromatic group, such as phenyl or naphthyl, or a substituted or unsubstituted heteroaromatic group containing one or more, preferably one, heteroatom, such as pyridyl, pyrrolyl, furanyl, thienyl, thiazolyl, isothiazolyl, oxazolyl, isoxazolyl, oxadiazolyl, thiadiazolyl pyrazolyl, imidazolyl, triazolyl, pyrimidinyl pyridazinyl, pyrazinyl, triazinyl, indolyl, indazolyl, quinolyl, quinazolyl, benzimidazolyl, benzothiazolyl, benzisoxazolyl and benzisothiazolyl.

The alkyl and aryl groups may be substituted or unsubstituted. Where substituted, there will generally be, for example, 1 to 3 substituents present, preferably 1 substituent. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, arloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted, preferably unsubstituted. Where substituted, there will generally be, for example, 1 to 3 substitutents present, preferably 1 substituent.

As used herein, the term "alkoxy" means, for example, alkyl-O— and "alkoyl" means, for example, alkyl-CO—. Alkoxy substituent groups or alkoxy-containing substituent groups may be substituted by, for example, one or more alkyl groups.

As used herein, the term "halogen" means, for example, a fluorine, chlorine, bromine or iodine radical, preferably a fluorine, chlorine or bromine radical, and more preferably a fluorine or chlorine radical.

"Pharmaceutically acceptable," such as pharmaceutically acceptable carrier, excipient, etc., means pharmacologically acceptable and substantially non-toxic to the subject to whom the particular compound is administered.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a well known technique which is used in attempting to improve properties involving physical or chemical stability, e.g., hygroscopicity, flowability or solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid. Examples of ester groups which are cleaved (in this case hydrolyzed) in vivo to the corresponding carboxylic acids are those in which the cleaved hydrogen is replaced with -lower alkyl which is optionally substituted, e.g., with heterocycle, cycloalkyl, etc. Examples of substituted lower alkyl esters are those in which -lower alkyl is substituted with pyrrolidine, piperidine, morpholine, N-methylpiperazine, etc. The group which is cleaved in vivo may be, for example, ethyl, morpholino ethyl, and diethylamino ethyl. In connection with the present invention, $-CONH_2$ is also considered an ester, as the $-NH_2$ is cleaved in vivo and replaced with a hydroxy group, to form the corresponding carboxylic acid.

Further information concerning examples of and the use of esters for the delivery of pharmaceutical compounds is available in Design of Prodrugs. Bundgaard H. ed. (Elsevier, 1985). See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. The therapeutically effective amount of the compounds of formula I can vary within wide limits depending on the disease to be controlled, the age and the individual condition of the patient and the mode of administration, and will, of course, be fitted to the individual requirements in each particular case. Preferably, the therapeutically effective amount may be from about 0.01 mg/kg to about 50 mg/kg per day, more preferably from about 0.3 mg/kg to about 10 mg/kg per day. The daily dosage can be administered as a single dose or in divided doses, or for parenteral administration it may be given as continuous infusion.

Compounds of the present invention can be prepared beginning with commercially available starting materials and utilizing general synthetic techniques and procedures known to those skilled in the art. Outlined below are preferred reaction schemes suitable for preparing such compounds. Further exemplification is found in the specific Examples detailed below.

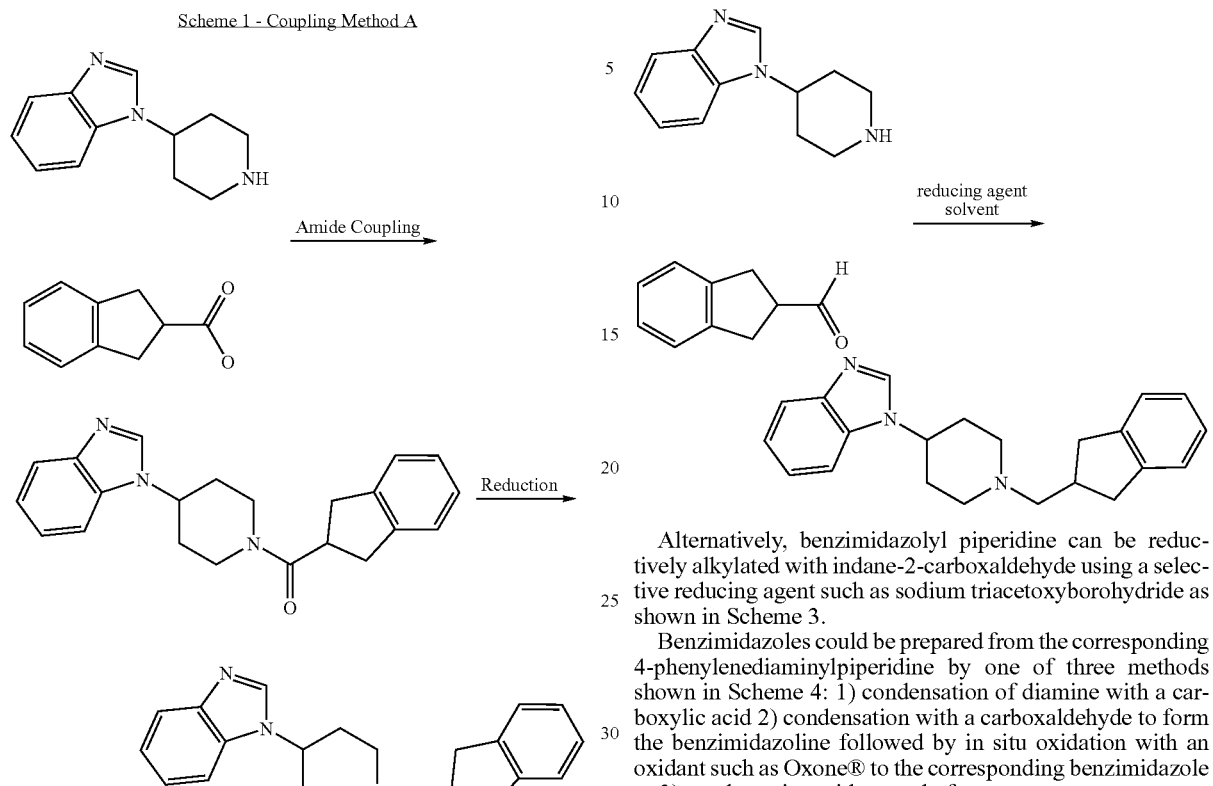

Benzimidazoylpiperines can be coupled to indane carboxylic acids via well-established coupling methodologies and the resulting amide can be reduced using borane or lithium aluminum hydride to yield an N-substituted piperidine.

Alternatively, iodomethyl- or bromomethylindane in the presence of a base such as potassium carbonate can be used to N-alkylate benzimidazolypiperidines as shown in scheme 2.

Alternatively, benzimidazolyl piperidine can be reductively alkylated with indane-2-carboxaldehyde using a selective reducing agent such as sodium triacetoxyborohydride as shown in Scheme 3.

Benzimidazoles could be prepared from the corresponding 4-phenylenediaminylpiperidine by one of three methods shown in Scheme 4: 1) condensation of diamine with a carboxylic acid 2) condensation with a carboxaldehyde to form the benzimidazoline followed by in situ oxidation with an oxidant such as Oxone® to the corresponding benzimidazole or 3) condensation with an orthoformate.

Indane carboxylic acids, indane carboxaldehydes and 2-iodomethylindanes can be purchased or prepared according to methods described in the chemical literature.

Preferred Intermediates

Preparation of
4-(2-amino-4-methyl-phenylamino)-Boc piperidine

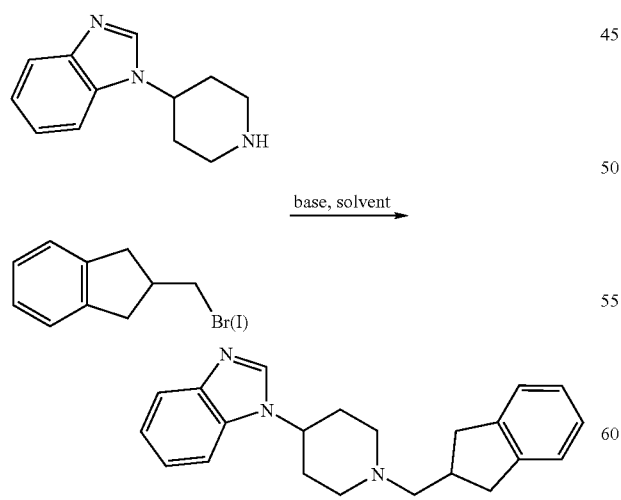

4-(2-amino-4-methyl-phenylamino)-Boc piperidine was synthesized from 4-amino Boc piperidine and 4-fluoro-3-nitrotoluene by methods analogous to those described by Henning et. al. *J. Med. Chem.* 1987, 30, 814-819. The following is an example:

4-(4-Methyl-2-nitro-phenylamino)-piperidine-1-carboxylic acid tert-butyl ester A mixture of 4-amino-1-Boc-piperidine (78 g; 390 mmol), 4-fluoro-3-nitrotoluene (50 g; 354 mmol), and $^i$Pr$_2$NEt (91.5 g; 708 mmol) in 1-butanol (1.5 L) was heated to reflux overnight. The solvent was removed under reduced pressure. The crude residue was purified by flash chromatography (CH$_2$Cl$_2$ to 1% CH$_3$OH in CH$_2$Cl$_2$) to provide 4-(4-methyl-2-nitro-phenylamino)-piperidine-1-carboxylic acid tert-butyl ester as an orange powder (76.3 g, 64%).

LRMS (M+1)—Calculated: 336.2. Found 336.2.

4-(2-amino-4-methyl-phenylamino)-piperidine-1-carboxylic acid tert-butyl ester

To a solution of 4-(4-methyl-2-nitro-phenylamino)-piperidine-1-carboxylic acid tert-butyl ester (9.5 g, 28.4 mmol) in ethanol (150 mL) was added 10% Pd/C (125 mg) and the reaction mixture was shaken under H$_2$ (50 psi) at rt for 1 h. The catalyst was then removed by filtration through a pad of Celite® and washed with ethanol. The filtrate was concentrated in vacuo to provide 4-(2-amino-4-methyl-phenylamino)-piperidine-1-carboxylic acid tert-butyl ester (7.83 g) in 90% yield.

LRMS (M+1)–Calculated: 306.2. Found 306.2.

$^1$H NMR (DMSO-d$_6$, 400 MHz) δ 6.40 (d, J=8 Hz, 1H), 6.37 (d, J=1.7 Hz, 1H), 6.28 (dd, J$_1$=1.7 Hz, J$_2$=8 Hz, 1H), 4.44 (s, 2H), 3.96 (d, J=8 Hz, 1H), 3.88 (brd, J=13 Hz, 2H), 3.32 (m, 1H), 2.88 (m, 2H), 2.07 (s, 3H), 1.88 (dd, J$_1$=3 Hz, J$_2$=13 Hz, 2H), 1.40 (s, 9H), 1.22 (m, 2H).

Preparation of a Racemic Mixture of (R)-4-(2-amino-4-methyl-phenylamino)-3-(R)-hydroxy-Boc piperidine and (S)-4-(2-amino-4-methyl-phenylamino)-3-(S)-hydroxy-Boc piperidine

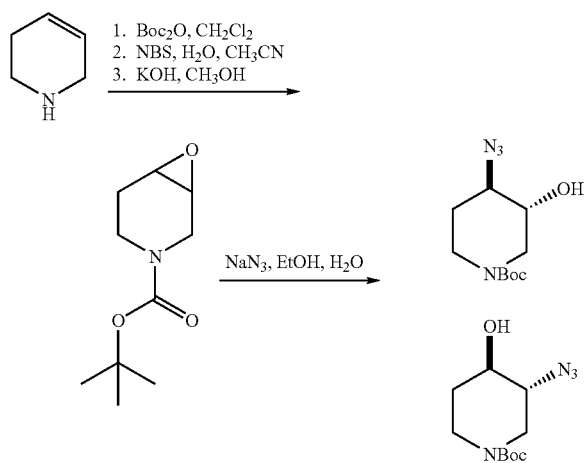

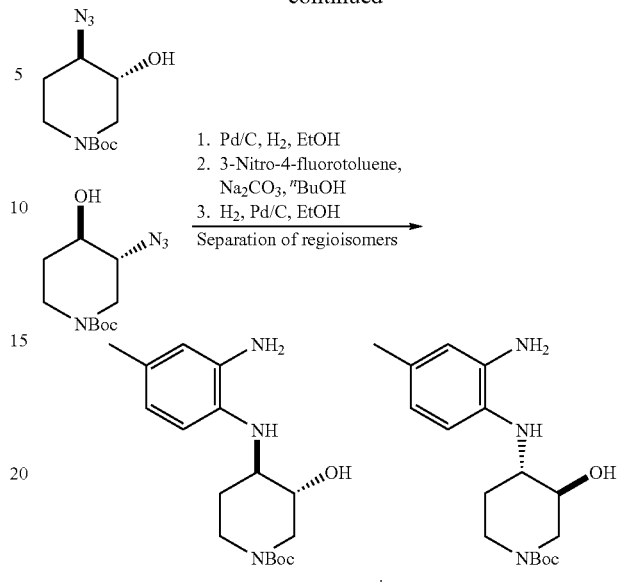

rac-4-(2-Amino-4-methyl-phenylamino)-3-(R)-hydroxy-Boc piperidine 1,2,3,6-Tetrahydropyridine (66 g; 795 mmol) in CH$_2$Cl$_2$ (2000 mL) was treated with di-tert-butyl dicarbonate (170 g; 780 mmol). Evolution of gas was observed. After 60 minutes all volatiles were removed in vacuo yielding N-Boc tetrahydropyridine as a light oil. N-Bromosuccinimide (214 g; 1200 mmol) was added portionwise over 20 minutes to a solution of N-Boc-dihydropyridine in water (600 mL) and CH$_3$CN (2400 mL) at 0° C. After 4 h at rt all volatiles were removed under reduced pressure and the reaction mixture was diluted with water (400 mL) and extracted three times with diethyl ether. The combined organic phases were washed with brine and dried over MgSO$_4$. Filtration followed by removal of volatiles under reduced pressure yielded an oily solid which was dissolved in CH$_3$OH and treated with aqueous KOH (1.0 M; 500 mL, 500 mmol). After stirring for one hour, all volatiles were removed under reduced pressure and the resulting solid was suspended in water (1000 mL) and extracted three times with CH$_2$Cl$_2$. The combined organic phases were dried over MgSO$_4$. Filtration and removal of volatiles under reduced pressure yielded crude epoxide as an oil (157.5 g; quantitative).

Crude epoxide (theoretical: 795 mmol) was dissolved in ethanol (270 mL) and water (2100 mL) and treated with NaN$_3$ (73.2 g; 1.12 mol). The resulting suspension was stirred for 20 h after which it was extracted three times with diethyl ether. The combined organic phases were washed twice with water, once with brine and dried over MgSO$_4$. Filtration followed by removal of volatiles under reduced pressure yielded a 4:1 mixture of 4-azido-3-hydroxy-Boc piperidine and 3-azido-4-hydroxy-Boc piperidine (174.6 g; 93% from 1,2,3,6-tetrahydropyridine).

A 4:1 mixture of racemic trans-4-azido-3-hydroxy-Boc piperidine and 3-azido-4-hydroxy-Boc piperidine (58 g; 252 mmol), 4-fluoro-3-nitrotoluene (60 g, 387 mmol) and Na$_2$CO$_3$ (85 g, 800 mmol) in 1-butanol was heated to reflux for 24 hr. The reaction mixture was then cooled and all volatiles were removed under reduced pressure. The resulting orange sludge was washed with hexane three times and dried in vacuo. The resulting solid was suspended in H$_2$O and the pH was adjusted to 7 with acetic acid. The suspension was stirred for 1 h and the product racemic 1-Boc-trans-3-methoxy-4-(4-methyl-2-nitro-phenylamino)-piperidine was collected by filtration as an orange solid and dried in vacuo (55.6 g, 63%).

A mixture of racemic 1-Boc-trans-3-hydroxy-4-(4-methyl-2-nitro-phenylamino)-piperidine (15.0 g, 42.6 mmol) and 10% Pd on carbon (1.5 g, 10% by weight) in ethanol (280 mL) was stirred under 1 atm of $H_2$ gas for 17 h. The solid catalyst was then removed by filtration through Celite and all volatiles were removed under reduced pressure to yield the product, racemic 1-Boc-trans-4-(2-amino-4-methyl-phenylamino)-3-hydroxy-piperidine as a heavy oil (14.1 g, quant).

LRMS (M+1)—Calculated: 322.2. Found: 322.2.

Chiral Resolution

Racemic 1-Boc-trans-4-(2-amino-4-methyl-phenylamino)-3-hydroxy-piperidine was resolved into RR and SS enantiomers via chiral chromatography. (PDR Chiral Inc., Lake Park, Fla.).

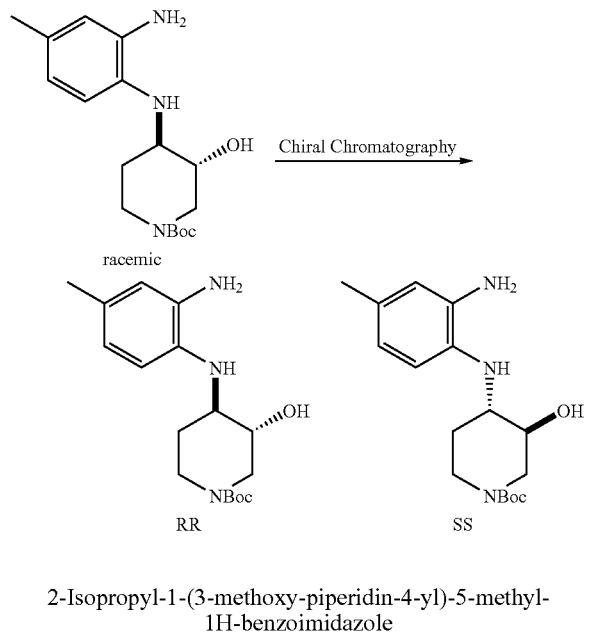

2-Isopropyl-1-(3-methoxy-piperidin-4-yl)-5-methyl-1H-benzoimidazole

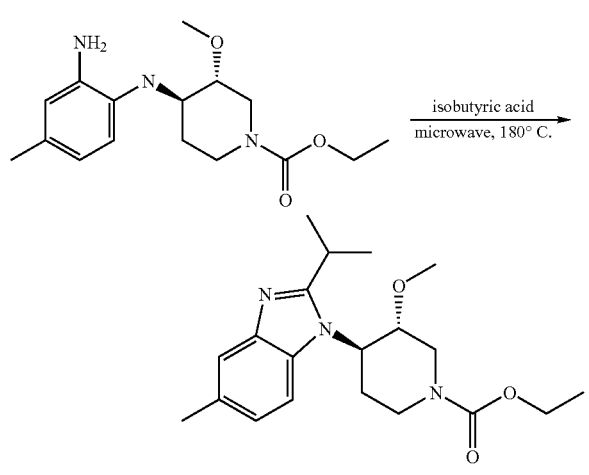

A solution of 4-(2-amino-4-methyl-phenylamino)-3-methoxy-piperidine-1-carboxylic acid ethyl ester (750 mg, 2.44 mmol) in isobutyric acid (15 mL) was subjected to microwave irradiation for 1 h with a resulting temperature of 180° C. The reaction mixture was cooled to rt and then diluted with $CH_2Cl_2$ (150 mL) and a saturated $NaHCO_3$ solution (200 mL). The aqueous layer was extracted twice with $CH_2Cl_2$. The combined organic extracts were dried over $Na_2SO_4$, filtered, and concentrated under reduced pressure. The residue was purified by flash chromatography (15/1 $CH_2Cl_2$/$CH_3OH$) to yield 4-(2-isopropyl-5-methyl-benzoimidazol-1-yl)-3-methoxy-piperidine-1-carboxylic acid ethyl ester (465 mg, 56%) as a waxy solid.

LRMS (M+1)—Calculated: 359.5. Found: 359.5.

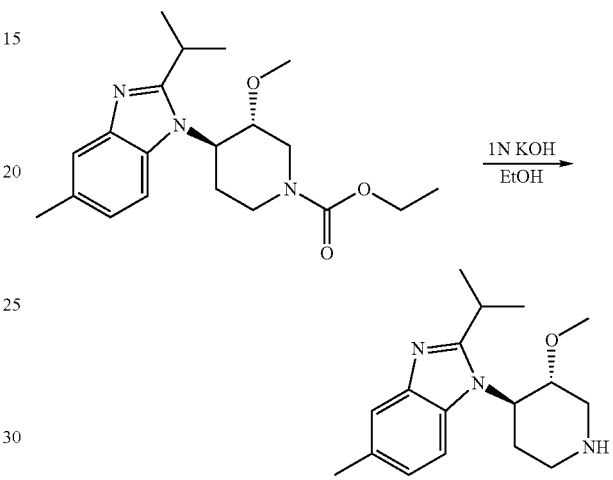

A solution of 4-(2-isopropyl-5-methyl-benzoimidazol-1-yl)-3-methoxy-piperidine-1-carboxylic acid ethyl ester (465 mg, 1.37 mmol) in a 1/1 1N KOH/EtOH solution (10 mL) was heated to 80° C. overnight. The mixture was concentrated under reduced pressure and the residue was purified by flash chromatography (15/1 $CH_2Cl_2$/$CH_3OH$) to yield 2-isopropyl-1-(3-methoxy-piperidin-4-yl)-5-methyl-1H-benzoimidazole (69 mg, 18%) as a white solid.

LRMS (M+1)—Calculated: 287.4. Found: 287.4.

2-Ethyl-1-(3-methoxy-piperidin-4-yl)-5-methyl-1H-benzoimidazole

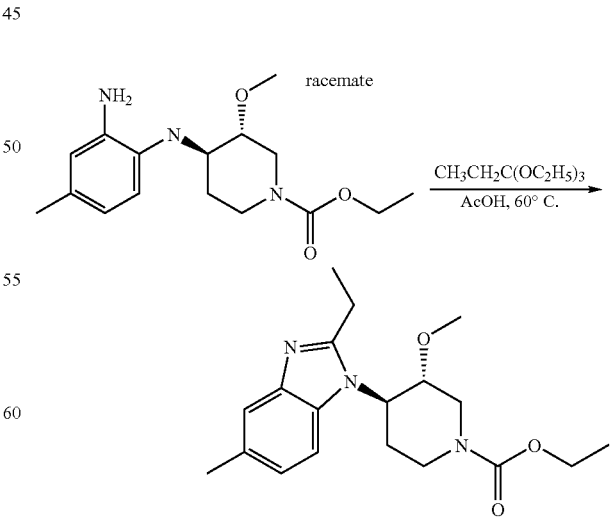

To a solution of 4-(2-amino-4-methyl-phenylamino)-3-methoxy-piperidine-1-carboxylic acid ethyl ester (800 mg, 2.60 mmol) in acetic acid (5 mL) was added 1,1,1-triethoxy ethane (550 mg, 3.12 mmol). After heating at 60° C. for 30 minutes, the mixture was concentrated under reduced pressure and the residue was purified by flash chromatography (15/1 CH$_2$Cl$_2$/CH$_3$OH) to 4-(2-ethyl-5-methyl-benzoimidazol-1-yl)-3-methoxy-piperidine-1-carboxylic acid ethyl ester (940 mg, 89%) as a white solid.

LRMS (M+1)—Calculated: 345.4. Found: 345.4.

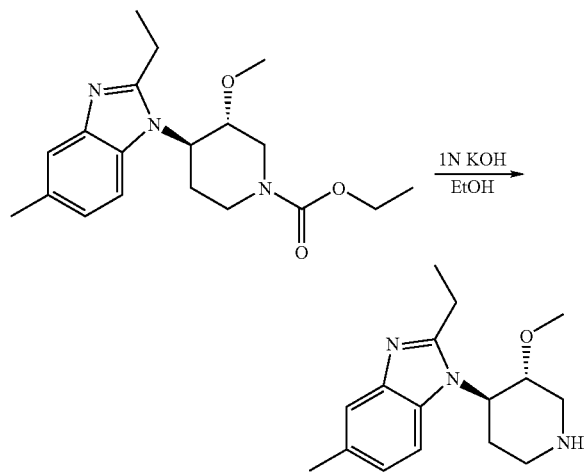

A solution of 4-(2-ethyl-5-methyl-benzoimidazol-1-yl)-3-methoxy-piperidine-1-carboxylic acid ethyl ester (940 mg, 3.08 mmgol) in a 1/1 1N KOH/EtOH (20 mL) solution was heated to 80° C. overnight. The mixture was concentrated under reduced pressure and the residue was purified by flash chromatography (15/1 CH$_2$Cl$_2$/CH$_3$OH) to 2-ethyl-1-(3-methoxy-piperidin-4-yl)-5-methyl-1H-benzoimidazole (132 mg, 16%) as a white solid.

LRMS (M+1)—Calculated: 273.4. Found: 273.4.

2-Cyclopropyl-1-(3-methoxy-piperidin-4-yl)-5-methyl-1H-benzoimidazole hydrochloride salt

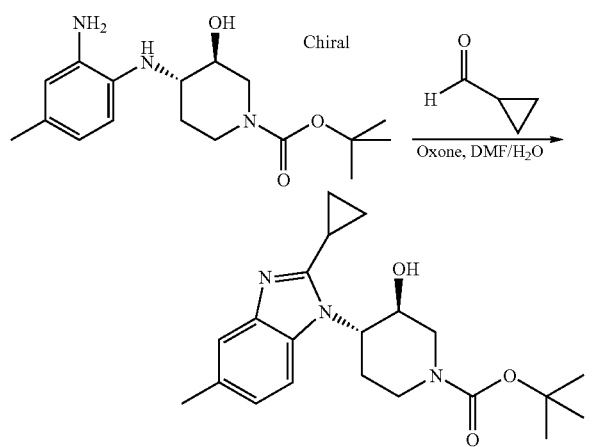

To a solution of 4-(2-amino-4-methyl-phenylamino)-3-hydroxy-piperidine-1-carboxylic acid tert-butyl ester (2 g, 6.23 mmol) and cyclopropanecarboxaldehyde (485 μL, 6.5 mmol) in a 3% H$_2$O/DMF (10 mL) solution was added Oxone® (3.05 g, 4.96 mmol). The mixture was stirred for 1 h and poured into a 0.2 N NaOH solution (25 mL). After stirring for 5 minutes, the aqueous layer was extracted four times with ethyl acetate. The combined organic extracts were washed twice with water, once with brine, dried over Na$_2$SO$_4$, filtered, and concentrated under reduced pressure. The residue was purified by flash chromatography (4/1 ethyl acetate/hexanes) to yield 4-(2-cyclopropyl-5-methyl-benzoimidazol-1-yl)-3-hydroxy-piperidine-1-carboxylic acid tert-butyl ester (860 mg, 37%).

LRMS (M+1)—Calculated: 371.5. Found: 371.5.

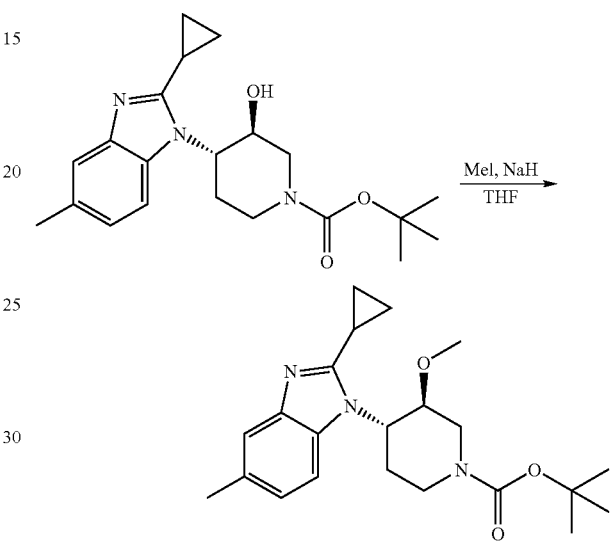

To a solution of 4-(2-cyclopropyl-5-methyl-benzoimidazol-1-yl)-3-hydroxy-piperidine-1-carboxylic acid tert-butyl ester (860 mg, 2.3 mmol) in dry THF (10 mL) at 0° C. was added NaH (60% dispersion in mineral oil, 129 mg, 3.22 mmol). After stirring for 20 minutes, methyl iodide (0.2 mL, 3.22 mmol) was added. After stirring for 15 minutes, the mixture was allowed to rt and stirred overnight. The mixture was diluted with ethyl acetate and quenched with water. The aqueous layer was extracted with ethyl acetate. The combined organic extracts were washed with water, brine, dried over Na$_2$SO$_4$, filtered, and concentrated under reduced pressure. The residue was purified by flash chromatography (2/3 ethyl acetate/hexanes) to 4-(2-cyclopropyl-5-methyl-benzoimidazol-1-yl)-3-methoxy-piperidine-1-carboxylic acid tert-butyl ester (650 mg, 73%).

LRMS (M+1)—Calculated: 385.5. Found: 385.5.

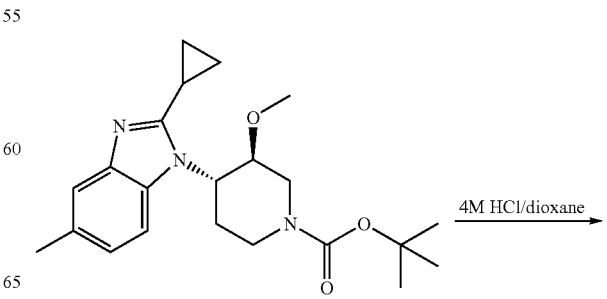

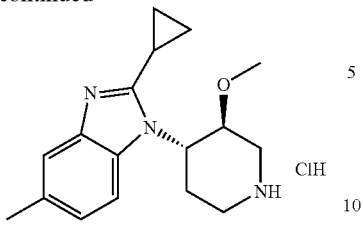

A solution of 4-(2-cyclopropyl-5-methyl-benzoimidazol-1-yl)-3-methoxy-piperidine-1-carboxylic acid tert-butyl ester (650 mg, 1.69 mmol) in a 4 M HCl/dioxane (3 mL) solution was stirred for 0.5 h. The solvent was removed to provide 2-cyclopropyl-1-(3-methoxy-piperidin-4-yl)-5-methyl-1H-benzoimidazole hydrochloride salt in quantitative yield without further purification.

LRMS (M+1)—Calculated: 285.4. Found: 285.4.

4-(5-Methyl-2-phenylbenzimidazolyl)-N-Boc piperidine

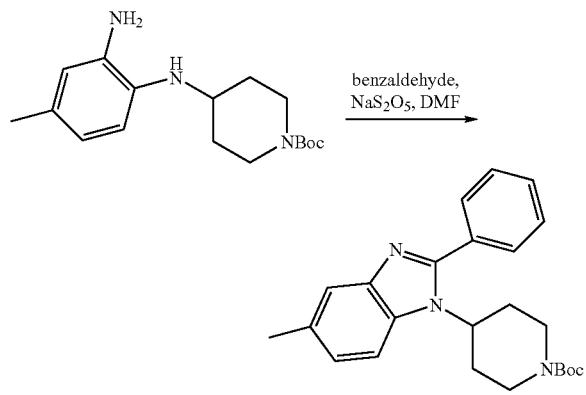

In a small pressure bottle was placed 4-(2-amino-4-methyl-phenylamino)-piperidine-1-carboxylic acid tert-butyl ester, benzaldehyde (92 µL, 0.90 mmol), sodium hydrogensulfite (147 mg, 1.48 mmol) in DMF (5 mL). The bottle was sealed and heated at 100° C. for two hours and then stirred at 25° C. overnight for 16 hours. The reaction mixture was then concentrated in vacuo and partitioned between ethyl acetate (15 mL) and brine/water (1:1, 15 mL). The organic phase was dried over $Na_2SO_4$, filtered and concentrated under reduced pressure. Flash chromatography (Biotage 40S column, 40/60 ethyl acetate/hexanes) afforded 4-(5-methyl-2-phenyl-benzoimidazol-1-yl)-piperidine-1-carboxylic acid tert-butyl ester (339 mg, quantitative) as a light purple foam.

LRMS (M+1)—Calculated: 392.2333. Found: 392.2332.

2-(5-Methyl-1-piperidin-4-yl-1H-benzoimidazol-2-yl)-propan-2-ol

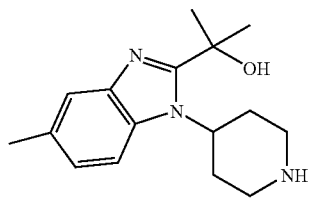

2-(5-Methyl-1-piperidin-4-yl-1H-benzoimidazol-2-yl)-propan-2-ol was prepared from 4-(2-amino-4-methyl-phenylamino)-piperidine-1-carboxylic acid tert-butyl ester and 2-hydroxyisobutyric acid according to the procedure described by Skolnik et. al. *J. Amer. Chem. Soc.*, 1943, 65, 1854-1858. The yields of the product after washing with water and drying varied from 78-87% as an off-white solid.

$^1$H NMR (DMSO-$d_6$, 300 MHz) δ 7.60, 7.36, 6.99, 5.63 (s, 1H), 5.30 (m, 1H), 3.10 (br m, 2H), 2.54 (br m, 2H), 2.37 (s, 3H), 2.22-2.36 (m, 3H), 1.74 (brd, 2H), 1.61 (s, 6H).

HRMS (M+1)—Calculated: 274.1914. Found: 274.1914.

Racemic trans-4-(2,5-Dimethylbenzimidazol-1-yl)-3-hydroxymethylpiperidine dihydrochloride

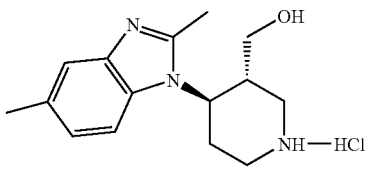

$NaCNBH_3$ (5.05 g; 110 mmol) and $NH_4OAc$ (8.25 g; 110 mmol) were added to a solution of N-Boc-3-ethylcarboxy-4-piperidone (3.0 g; 11 mmol) in ethanol (100 mL) under Ar. The mixture was heated to reflux for 2 hours then cooled to rt. Solids were removed by filtration through a bed of Celite® and all volatiles were removed under reduced pressure. The resulting gummy solid was suspended in EtOAc and washed once with saturated $Na_2CO_3$ and once with brine. The organic phase was dried over $Na_2SO_4$. Filtration to removed solids followed by removal of volatiles under reduced pressure yielded N-Boc-3-carboxyethyl-4-aminopiperidine (2.17 g; 72%) as an oil.

4-Fluoro-3-nitrotoluene (2.63 g; 17 mmol), N-Boc-3-carboxyethyl-4-aminopiperidine (3.7 g; 13.55 mmol) and $Na_2CO_3$ (27 mmol) in 1-butanol (40 mL) were heated to reflux for 18 h. The reaction mixture was then cooled and solids were removed by filtration. Removal of volatiles under reduced pressure followed by flash chromatography (15-25% ethyl acetate in hexane) yielded racemic trans-4-(4-methyl-2-nitrophenylamino)-3-ethoxycarbonyl-4-Boc piperidine as an orange oil (1.23 g, 22%).

4-(4-Methyl-2-nitrophenylamino)-3-ethoxycarbonyl-4-Boc piperidine (1.20 g; 2.94 mmol) and 10% Pd/C (200 mg) were added to ethanol (20 mL) and the reaction mixture was shaken under hydrogen pressure (60 psi) for 1 h. The reaction mixture was evacuated and purged with nitrogen. The solids were removed by filtration through a bed of Celite® and volatiles were removed under reduced pressure. The resulting brown oil was dissolved in acetic acid (12 mL) and trimethyl orthoacetate (3 mL). The reaction mixture was heated to 100° C. for 1 h. After cooling, all volatiles were removed under reduced pressure and racemic trans-4-(2,5-dimethylbenzimidazol-1-yl)-3-carboxyethyl-N-Boc piperidine.

Lithium aluminum hydride (76 mg; 2 mmol) was added to a stirring solution of 4-(2,5-dimethylbenzimidazol-1-yl)-3-carboxyethyl-N-Boc piperidine (310 mg; 0.77 mmol) in THF (5 mL) under Ar at 0° C. After one hour, $Na_2SO_4$ decahydrate (500 mg; 1.55 mmol) was added carefully portionwise. The reaction mixture was stirred 2 h and the grey solid that formed during this time was removed by filtration through Celite®. Volatiles were removed under reduced pressure and the product racemic trans-4-(2,5-dimethylbenzimidazol-1-yl)-3-hydroxymethyl-N-Boc piperidine was isolated by flash chromatography (258 mg; 93%) as a white powder.

Racemic trans-4-(2,5-Dimethylbenzimidazol-1-yl)-3-hydroxymethyl-N-Boc piperidine (250 mg; 0.70 mmol) was dissolved in 4M HCl in dioxane for 60 min. All volatiles were then removed under reduced pressure and the resulting sticky solid was triturated with diethyl ether to yield racemic trans-4-(2,5-dimethylbenzimidazol-1-yl)-3-hydroxymethylpiperidine dihydrochloride as a white solid (231 mg; quant.).

LRMS (M+1)—Calculated: 259.2. Found: 259.1.

Preparation of racemic trans-3-[2-Hydroxy-2-methylpropoxy]-4-[2,5-dimethylbenzimidazol-1yl]-piperidine dihydrochloride

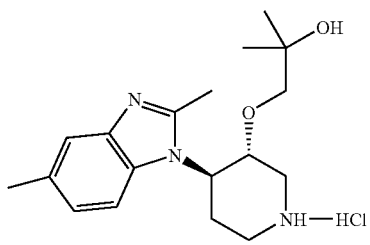

A stirring solution of racemic trans-3-hydroxy-4-[2,5-dimethylbenzimidazol-1yl]-N-Boc-piperidine (950 mg; 2.75 mmol) in THF (30 mL) under Ar cooled to 0° C. NaH (60% oil dispersion; 132 mg; 3.3 mmol) was added and the mixture was stirred for 15 min followed by addition of tert-butyl bromoacetate (516 µL; 3.5 mmol). The reaction mixture was warmed to rt and allowed to stir for 14 hours after which it was poured into satd NH$_4$Cl and extracted three times with ethyl acetate. The combined organic layers were washed with brine and dried over MgSO$_4$. Filtration followed by removal of volatiles under reduced pressure yielded crude product. Racemic 3-tert-butoxycarbonylmethoxy-4-(2,5-dimethyl-benzoimidazol-1-yl)-piperidine-1-carboxylic acid tert-butyl ester was isolated as an oil by flash chromatography (470 mg; 37%)

Racemic 3-tert-butoxycarbonylmethoxy-4-(2,5-dimethyl-benzoimidazol-1-yl)-piperidine-1-carboxylic acid tert-butyl ester (470 mg; 1.02 mmol) in THF (10 mL) was treated with CH$_3$MgBr (1.0 M in THF; 3 mL, 3 mmol). The reaction mixture was allowed to stir for 1 h and then poured into saturated NH$_4$Cl and extracted three times with ethyl acetate. The combined organic layers were washed with brine and dried over MgSO$_4$. Filtration followed by removal of volatiles under reduced pressure yielded crude product. trans-3-[2-Hydroxy-2-methylpropoxy]-4-[2,5-dimethylbenzimidazol-1yl]-N-Boc-piperidine was isolated by flash chromatography as an oil (324 mg; 78%).

Racemic trans-3-[2-hydroxy-2-methylpropoxy]-4-[2,5-dimethylbenzimidazol-1yl]-N-Boc-piperidine (320 mg; 0.77 mmol) was treated with 4M HCl in dioxane for 1 h after which all volatiles were removed under reduced pressure to yield the product trans-3-[2-hydroxy-2-methylpropoxy]-4-[2,5-dimethylbenzimidazol-1yl]-piperidine dihydrochloride (300 mg; quant.). LRMS (M+1)—Calculated: 317.2. Found: 317.2.

4-(5-fluoro-2-methylbenzimidazol-1-yl)-3-methoxy-piperidine dihydrochloride

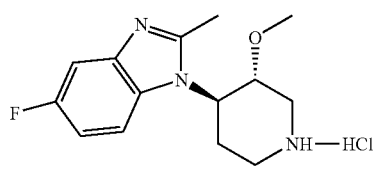

A mixture of racemic trans-3-hydroxy-4-amino-Boc-piperidine (3.90 g, 18.05 mmol), 2,5-difluoronitrobenzene (3.5 g, 22 mmol) and Na$_2$CO$_3$ (3.18 g; 30 mmol) in 1-butanol (100 mL) was heated to 90° C. for 16 h. The reaction mixture was then cooled and solids removed by filtration through Celite®. The reaction mixture was concentrated in vacuo and the product racemic trans-4-(4-fluoro-2-nitrophenylphenylamino)-3-hydroxy-Boc-piperidine as an orange solid (4.56 g; 78%).

Racemic trans-4-(4-Fluoro-2-nitrophenylphenylamino)-3-hydroxy-Boc-piperidine (4.5 g; 12.85 mmol) and 10% Pd/C (500 mg) were shaken in ethanol (100 mL) under hydrogen pressure (60 psi) for 2 h. The catalyst was then removed by filtration through Celite®. All volatiles were removed under reduced pressure to yield the reduction product as a tan foam which was used without further purification.

The product diamine was dissolved in acetic acid (30 mL) and trimethyl orthoacetate (10 mL) and heated to 70° C. for 1 h. The reaction mixture was then cooled to rt and all volatiles were removed to yield a brown foam from which the product 4-(5-fluoro-2-methylbenzimidazol-1-yl)-3-hydroxy-Boc-piperidine was isolated by flash chromatography (ethyl acetate) as a tan foamy solid (2.74 g, 61%).

4-(5-fluoro-2-methylbenzimidazol-1-yl)-3-hydroxy-Boc-piperidine (205 mg, 0.59 mmol) mmol) in THF (5 mL) and cooled to 0° C. under Ar. NaH (60% oil dispersion; 32 mg, 0.8 mmol) was added and the reaction mixture was stirred for 15 minutes. Iodomethane (0.8 mmol) was then added. After stirring for 3 hours at rt the reaction mixture was poured into saturated NaHCO$_3$ and extracted three times with ethyl acetate. The combined organic layers were washed with brine and dried over MgSO$_4$. Filtration followed by removal of volatiles under reduced pressure yielded crude product from which 4-(5-fluoro-2-methylbenzimidazol-1-yl)-3-methoxy-Boc-piperidine (191 mg, 89%) was isolated as a waxy solid.

4-(5-fluoro-2-methylbenzimidazol-1-yl)-3-methoxy-Boc-piperidine (185 mg, 0.23 mmol) was dissolved in 4M HCl in dioxane and stirred for 90 minutes after which all volatiles were removed under reduced pressure. The resulting gummy solid was triturated with diethyl ether to yield 4-(5-fluoro-2-methylbenzimidazol-1-yl)-3-methoxy-piperidine dihydrochloride as an off-white solid (76 mg, quant.).

LRMS (M+1)—Calculated: 263.1. Found: 263.2.

N-{(R)-2-[4-(2,5-Dimethyl-benzoimidazol-1-yl)-3-hydroxy-piperidine dihydrochloride

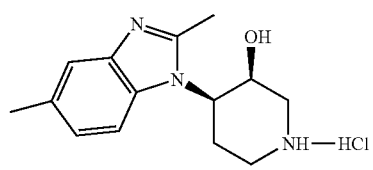

Racemic cis-3-amino-4-amino-N-ethoxycarbonylpiperidine was prepared according to the method described by Kim et. al. *Syn. Comm.* 2001, 31, 1081-89. Arylation with 4-fluoro-3-nitrotoluene and subsequent conversion to 2,5-dimethylbenzimidazole was effected according to methods described above. Removal of the ethyl carbamate protecting group was carried out by conventional methods, Morice et. al. *Tetrahedron Letters* 2001, 42(37), 6499-6502

19

1-(5-Methyl-1-piperidin-4-yl-1H-benzoimidazol-2-yl)-ethanone

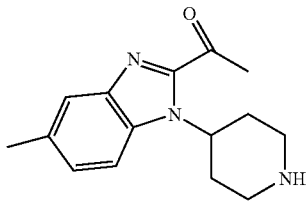

p-Nitrophenyl 2,2-diethoxyproprionate was prepared by the method described by J. L. LaMattina and David E. Muse. *J. Org. Chem.*, 52, 3479 (1987).

4-(2-Amino-4-methyl-phenylamino)-piperidine-1-carboxylic acid tert-butyl ester (400 mg, 1.31 mmol), p-nitrophenyl 2,2-diethoxyproprionate (1.00 g, 3.50 mmol), and DMAP (1.00 g, 8.2 mmol) were combined in acetonitrile (3 mL) and heated in an oil bath at 80° C. for 2 h. The mixture was cooled, diluted with diethyl ether (100 mL), washed once each with saturated aqueous $NH_4Cl$ and water, three times with 5% aqueous sodium hydroxide solution, once with brine and dried over anhydrous $MgSO_4$ and concentrated under reduced pressure. The residue was adsorbed on a silica gel pad, and the pad was eluted with 25% ethyl acetate in hexanes to give 4-[2-(2,2-diethoxy-propionylamino)-4-methyl-phenylamino]-piperidine-1-carboxylic acid tert-butyl ester (550 mg, 0.81 mmol, 62%) of a pale yellow oil.

4-[2-(2,2-Diethoxy-propionylamino)-4-methyl-phenylamino]-piperidine-1-carboxylic acid tert-butyl ester (500 mg, 1.11 mmol) was dissolved in glacial acetic acid (5 mL), and the mixture was heated at 90° C. overnight. The mixture was cooled, concentrated under reduced pressure. The resulting residue was partitioned between $CH_2Cl_2$ (50 mL) and dilute aqueous $K_2CO_3$ solution. The organic layer was separated, and the aqueous layer was extracted with $CH_2Cl_2$ (2×25 mL). The combined organic layers were dried over anhydrous $Na_2SO_4$ and filtered. The filtrate was concentrated to approximately 30 mL, and di-tert-butyldicarbonate (218 mg, 1 mmol) and DMAP (5 mg, 0.04 mmol) were added. The mixture was stirred overnight at rt, washed with saturated aqueous $NH_4Cl$ solution and dried over anhydrous $Na_2SO_4$. The mixture was concentrated, and the residue was purified by flash chromatography (30% ethyl acetate in hexanes) to give 4-(2-acetyl-5-methyl-benzoimidazol-1-yl)-piperidine-1-carboxylic acid tert-butyl ester (270 mg, 0.756 mmol, 68%) as a waxy solid.

$^1$H-NMR (300 MHz, $CDCl_3$): δ=7.66 (s, 1H), 7.49 (d, 1H), 7.20 (dd, 1H), 5.73 (m, 1H), 4.34 (br. m, 3H), 2.91 (br. t, 1H), 2.85 (s, 3H), 2.48 (s, 3H), 2.41 (br. q, 1H), 1.91 (br. d, 2H), 1.52 (s, 9H).

4-(2-acetyl-5-methyl-benzoimidazol-1-yl)-piperidine-1-carboxylic acid tert-butyl ester (107 mg, 0.30 mmol) was dissolved in a mixture of trifluoroacetic acid (2 mL) and $CH_2Cl_2$ (2 mL) at rt and stirred for 1 hour. The mixture was concentrated under reduced pressure and the residue was partitioned between dilute aqueous $K_2CO_3$ solution (20 mL) and $CH_2Cl_2$ (20 mL). The organic layer was separated, and the aqueous layer was extracted with $CH_2Cl_2$ (2×15 mL). The combined organic layers were dried over anhydrous $Na_2SO_4$ and concentrated under reduced pressure to give 1-(5-methyl-1-piperidin-4-yl-1H-benzoimidazol-2-yl)-ethanone as an oil (77 mg, 0.30 mmol, 100%) that was used without further purification or characterization.

20

2,6-Dimethyl-3-piperidin-4-yl-3H-imidazo[4,5-c]pyridine

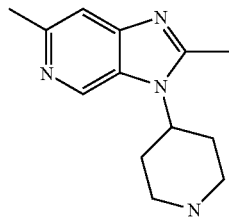

A solution of 5-bromo-2-methyl-pyridine (1.47 g, 8.54 mmol) in $CH_2Cl_2$ (5 mL) was treated with a cold solution of 30% hydrogen peroxide (4.6 mL) in acetic acid (13.8 mL) at 0° C. The reaction mixture was stirred at 50° C. for 18 h and poured into ice water (5 mL). The resulting mixture was adjusted to pH=9 by addition of $K_2CO_3$. The mixture was stirred at rt for 15 min and diluted with $CH_2Cl_2$ (10 mL). The aqueous layer was extracted three times with $CH_2Cl_2$. The combined extracts were washed with brine, dried over anhydrous $Na_2SO_4$, filtered and concentrated under reduced pressure to afford 5-bromo-2-methyl-pyridine N-oxide as a white solid (1.6 g, 99%) which was used without further purification.

A solution of 5-bromo-2-methyl-pyridine N-oxide (536 mg, 2.85 mmol) in concentrated $H_2SO_4$ (3.0 mL) was added dropwise a solution of fuming $HNO_3$ (2.4 mL) in concentrated $H_2SO_4$ (3.2 mL) at 0° C. The reaction mixture was heated at 90° C. for 1.5 h. The reaction mixture was cooled to rt and poured into ice (50 g). The mixture was extracted with $CH_2Cl_2$ (3×20 mL). The combined extracts were washed with brine, dried over anhydrous $Na_2SO_4$, filtered and concentrated under reduced pressure to afford 5-bromo-2-methyl-4-nitro-pyridine N-oxide as a yellow solid (520 mg, 78%) which was used without further purification 5-Bromo-2-methyl-4-nitro-pyridine N-oxide (520 mg, 2.23 mmol) was mixed with 4-amino-piperidine-1-carboxylic acid tert-butyl ester (1.56 g, 7.80 mmol) in a microwave tube. The reaction mixture was irradiated in a microwave oven at 140° C. for 1 h. The mixture was dissolved in $CH_2Cl_2$ (5 mL). Flash chromatography (10/1 $CH_2Cl_2/CH_3OH$) afforded 4-(6-methyl-4-nitro-pyridin-N-oxide-3-ylamino)-piperidine-1-carboxylic acid tert-butyl ester (380 mg, 48%) as a red solid.

A solution of 4-(6-methyl-4-nitro-pyridin-N-oxide-3-ylamino)-piperidine-1-carboxylic acid tert-butyl ester (40 mg, 0.113 mmol) in acetic acid (1 mL) was treated with iron powder (80 mg). The reaction mixture was stirred at 115° C. for 5 h and then was treated with acetic anhydride (2 mL). The resulting mixture was heated at 140° C. for 18 h. The solvent was evaporated and the mixture was diluted with water (10 mL). The mixture was adjusted to pH=10 by addition of solid sodium hydroxide. The aqueous mixture was extracted three times with $CH_2Cl_2$. The combined extracts were washed with brine, dried over anhydrous $Na_2SO_4$, filtered and concentrated under reduced pressure. Flash chromatography (10/1 $CH_2Cl_2/CH_3OH$) afforded 1-[4-(2,6-dimethyl-imidazo[4,5-c]-pyridin-3-yl)-piperidin-1-yl]-ethanone (20 mg, 65%) as a brown solid.

A solution of 1-[4-(2,6-dimethyl-imidazo[4,5-c]-pyridin-3-yl)-piperidin-1-yl]-ethanone (20 mg, 0.074 mmol) in ethanol (0.5 mL) was treated with concentrated HCl (0.5 mL). The reaction mixture was heated at 100° C. for 18 h. The solvent was evaporated and the mixture was diluted with water (2 mL). The mixture was washed twice with diethyl ether and the aqueous phase was adjusted to pH=10 by addition of a solution of 25% aqueous NaOH. The aqueous mixture was extracted with $CH_2Cl_2$ (5×10 mL). The combined extracts were washed with brine, dried over anhydrous $Na_2SO_4$, filtered and concentrated in vacuo to afford 2,6-dimethyl-3-piperidin-4-yl-3H-imidazo[4,5-c]pyridine (13 mg, 77%) as a light yellow solid which was used without further purification.

$^1$H-NMR (300 MHz, $CDCl_3$): δ 8.85 (s, 1H), 7.41 (s, 1H), 4.25 (m, 1H), 3.34 (d, 2H, J=10.2 Hz), 2.82 (t, 2H, J=12.3 Hz), 2.65 (s, 3H), 2.35 (m, 2H), 1.93 (d, 2H, J=10.2 Hz).

((S)-2-Iodomethyl-indan-5-yl)-carbamic acid tert-butyl ester

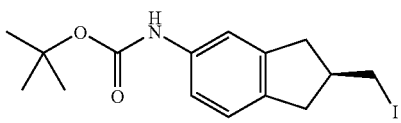

5.0 g (21 mmol) of 5-Bromo-1H-indene-2-carboxylic acid (5.0 g, 21 mmol) was suspended with stirring in a solution of $CH_3OH$ (200 mL) and THF (20 mL) in a Parr hydrogenation bottle and the mixture was warmed to ~40-42° C. Complete dissolution occurred within 5 minutes. The solution was cooled to rt and Argon gas was bubbled into the reaction solution. The flask was equipped with a septum and glass pipette for gas entry and equipped with a needle to permit the venting of exit gases. Care was taken not to change the composition of the solvents through evaporation by too rapid an introduction of argon. This process was continued for five minutes. $Ru(OAc)_2$[(S)-BINAP] (125 mg, 0.15 mmol), was added under argon; the flask was evacuated and refilled with hydrogen three times and hydrogenated by shaking at 52-54 psi at rt for 64 hours. The hydrogenation was discontinued and the reaction mixture evaporated to dryness. The residue was partitioned with water (25 mL) and ethyl ether (25 mL). The stirring mixture was brought to pH 10.8 by the addition of 15% aqueous NaOH (~4 mL). The aqueous phase was cooled with stirring in an ice-bath to 2-3° C. Concentrated aqueous HCl was added to pH 1.88 (~1.2 mL). Copious solids resulted. The mixture was extracted three times with ethyl ether. The combined extracts were washed with brine and dried from $MgSO_4$. Filtration followed by removal of volatiles under reduced pressure provided 4.78 g of a grey-white solid. The solid was dissolved in $CH_3OH$ (10 mL), warmed to 40° C. and a solution of (R)-α-methylbenzylamine (2.3 g, 18.98 mmol) in 5 mL of $CH_3OH$ was added. The vigorously stirred solution was brought to 68° C. in an oil-bath and the volume reduced to 5-7 mL. 30 mL of ethyl ether was added all at once and the mixture set aside to slowly cool and crystallize. After 2 h the solids were filtered and washed with ethyl ether to provide, after drying on the filter paper, 4.75 g white crystals. A second crop of crystals gave 0.98 g. The first crop was suspended in ethyl ether (50 mL) and stirred with 1N HCl (25 mL) until both layers were clear. The phases were separated and the aqueous phase was extracted three times with diethyl ether. Each extract washed in turn with brine. The extracts were combined and dried from $MgSO_4$, filtered and evaporated to yield 3.1 g of (S)-5-Bromoindane-2-carboxylic acid as a white solid. $[α]^D{}_{589}$=+24.88 (0.82%, $CH_3OH$) Chiral hplc indicated ~96.5 to 100% e.e. The second crop of crystals was treated in the same way to provide a small amount of acid with similar characteristics to the first material obtained.

Preparation of ((S)-5-Bromo-indan-2-yl)-methanol (S)-5-Bromo-indan-2-carboxylic acid (12.65 mmol) was dissolved in dry THF (75 mL). The mixture was cooled with stirring to 0-2° C. under argon. 1M $BH_3$ in THF (18.4 mL; 18.4 mmol) was added via syringe at a rapid dropwise rate. The mixture was stirred at 0° C. for 30 minutes then allowed to warm to rt and stir for 90 minutes. The reaction mixture was cooled again to 0° C. and treated carefully with 10 mL of water. Volatiles were removed under reduced pressure and the residue partitioned between diethyl ether (100 mL) and brine (50 mL). The aqueous phase was extracted with 100 mL ethyl ether and each extract washed with brine. The combined extracts were dried over $Na_2SO_4$, filtered and volatiles were removed under reduced pressure to give 2.85 g of ((S)-5-bromo-indan-2-yl)-methanol as a crystalline white solid.

$^1$H-NMR ($CDCl_3$) δ 7.23 (s, 1H), 7.20 (d, 1H), 6.98 (d, 1H), 3.61 (t, 2H), 3.00 (m, 2H), 2.68 (m, 3H), 1.41 (br s, 1H).

Preparation of ((S)-2-Hydroxymethyl-indan-5-yl)-carbamic acid tert-butyl ester ((S)-5-Bromo-indan-2-yl)-methanol (1.45 g, 6.38 mmol) was dissolved in toluene (12 mL) and argon gas bubbled through the solution for 10 minutes. To the stirring mixture was added, in the following order: tert-butyl carbamate (1.25 g, 10.67 mmol), copper(I) iodide (255 mg, 1.33 mmol), $K_2CO_3$ (2.46 g, 17.8 mmol) and finally N,N'-dimethylethylene-1,2-diamine (285 μL, 2.61 mmol). The mixture was mechanically stirred under argon at 110° C. After 18 hours, tlc monitoring of the reaction showed remaining starting material, the following additional reagents were added: tert-butyl carbamate (125 mg, 1.06 mmol), copper(I) iodide (25 mg, 0.13 mmol), potassium carbonate (250 mg, 1.8 mmol) and N,N'-dimethylethylene-1,2-diamine (30 μL, 0.27 mmol). Heating at 110° C. was continued for 2 hours after which the reaction mixture was cooled, solids removed by filtration and the filtrate evaporated, dissolved in a minimum amount of $CH_2Cl_2$ and purified by flash chromatography (ethyl ether). A crude product was obtained which was crystallized from 1:1 diethyl ether:hexane to give ((S)-2-Hydroxymethyl-indan-5-yl)-carbamic acid tert-butyl ester (410 mg, 24%) of white crystals. The mother liquor, comprised of a mixture of desired product and starting material was reserved to be reacted again.

((S)-2-Iodomethyl-indan-5-yl)-carbamic acid tert-butyl ester

The aforementioned (S)-2-hydroxymethyl-indan-5-yl-carbamic acid tert-butyl ester (2.15 g, 8.16 mmol) was dissolved in 50 mL of $CH_2Cl_2$. p-Toluenesulfonyl chloride (1.63 g, 8.54 mmol) and DMAP (1.1 g, 9.0 mmol) were added and the solution was stirred for 22 hours at rt. The reaction mixture was diluted with 50 mL of $CH_2Cl_2$ and washed in turn with saturated aqueous $NH_4Cl$, saturated aqueous $NaHCO_3$ and brine (100 mL each). Each wash was extracted with a small portion of $CH_2Cl_2$. The extracts were combined, dried over $Na_2SO_4$, filtered and evaporated. The residue was dissolved in warm ethyl ether (25 mL) and allowed to crystallize. The solid was filtered, washed with cold ethyl ether and dried to provide a beige solid as toluene-4-sulfonic acid (S)-5-tertbutoxycarbonylamino-indan-2-ylmethyl ester (2.1 g, 86%). $^1$H-NMR and MS data were compatible with the structure.

Toluene-4-sulfonic acid (S)-5-tert-butoxycarbonylamino-indan-2-ylmethyl ester (2.93 g, 7.02 mmol) was dissolved in DMF (60 mL) and heated and stirred at 70° C. with lithium iodide (4.7 g, 35.1 mmol) for 18 hours. Volatiles were removed under reduced pressure and the resulting residue was stirred with 100 mL of $CH_2Cl_2$ and solids removed by filtration. The filtrate was again evaporated, the residue was purified by flash column chromatography (10% of ethyl ether in hexanes) to yield a white solid as (S)-2-iodomethyl-indan-5-yl-carbamic acid tert-butyl ester (2.05 g, 78.5%).

$[\alpha]^D_{589}$=+16.48 (0.825%, $CH_3OH$).

LRMS (M+1)—Calculated: 374.2. Found: 374.1.

(R)-2-iodomethyl-indan-5-yl-carbamic acid tert-butyl ester was also prepared by using the same procedure with chiral ruthenium catalyst, $Ru(OAc)_2$[(R)-BINAP].

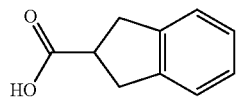

Prepared by the procedure of T. Tomiyama, S. Wakabayashi, and M. Yokota. *J. Med. Chem.*, 32, 1988 (1989).

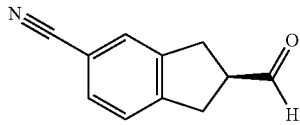

The (S)-5-bromoindan-2-yl-methanol (600 mg, 2.64 mmol) was mixed with zinc cyanide (480 mg, 4.09 mmol) in DMF (15 mL). To this solution was added palladium tetrakistriphenylphosphine (180 mg, 0.15 mmol). The mixture was heated in a microwave at 175° C. for 20 minutes. Solvents were evaporated and the residue was extracted with ethyl acetate and 0.1N hydrochloric acid. The organic layer was washed with brine and dried over $Na_2SO_4$. Solvents were evaporated and the residue was purified through a Biotage flash column chromatography using hexanes and ethyl acetate (2:1 to 1:1 ratio) to give (S)-5-cyanoindan-2-yl-methanol as a colorless oil (357 mg, 78%). Chiral HPLC analysis indicated no racemization.

$^1$H-NMR ($CDCl_3$) δ 7.24 (s, 1H), 7.20 (d, 1H), 7.00 (d, 1H), 3.38 (br s, 2H), 2.83 (m, 2H), 2.56 (m, 3H), 1.43 (br s, 1H); LRMS (M+1)—Calculated: 174.1. Found: 174.1.

The above (S)-5-cyanoindan-2-yl-methanol (132 mg, 0.76 mmol) was dissolved in 10 mL of $CH_2Cl_2$. To this solution was added Dess-Martin periodinane (334 mg, 0.79 mmol) at 0° C. The solution was stirred at 0° C. for one minute and ice bath was removed. After stirring at rt for 10 minutes, the reaction mixture was extracted with $CH_2Cl_2$ and concentrated $NaHCO_3$ solution. The organic layer was dried and solvents were evaporated. The residue was dried and then a mixture of ether and petroleum ether (20 mL, 1.5:1 ratio) was added. The solid was filtered and the filtrate was concentrated to give (S)-5-cyanoindan-2-yl-carboxaldehyde as an oil (114 mg, 88%). The chiral aldehyde was used without further purification.

Preparation of ((S)-5-Bromo-indan-2-yl)-aldehyde

Dess-Martin periodinane (2.70 g, 6.36 mmol) was added to a solution of (S)-5-bromoindan-2-yl-methanol (1.38 g, 6.08 mmol) in $CH_2Cl_2$ (75 mL) at 0° C. The ice bath was removed and the mixture was stirred at rt for 75 minutes. The mixture was extracted with $CH_2Cl_2$ and concentrated $NaHCO_3$ solution. The organic layer was washed with brine and dried over $Na_2SO_4$. Solvents were evaporated and the residue was dried in vacuo to give a semi-waxy material. This material was triturated with a mixture of ether and petroleum ether (60 mL, 1:1 ratio). The precipitate was removed by filtration and the filtrate was concentrated. The oily material was treated with a mixture of ether and petroleum ether (1:1 ratio, 30 mL). Again, solid was removed by filtration and the filtrate was concentrated to give (S)-5-bromoindan-2-yl-carboxaldehyde as an oil which gradually solidified when stored cold (1.335 g, 97.6%).

$^1$H-NMR ($CDCl_3$) δ 9.61 (s, 1H), 7.23 (s, 1H), 7.20 (d, 1H), 7.00 (d, 1H), 3.05-3.30 (m, 5H).

The invention will now be further described in the Examples below, which are intended as an illustration only and do not limit the scope of the invention.

EXAMPLES

Example 1

1-[(3R,4R)-1-((S)-5-Bromo-indan-2-ylmethyl)-3-methoxy-piperidin-4-yl]-2,5-dimethyl-1H-benzoimidazole

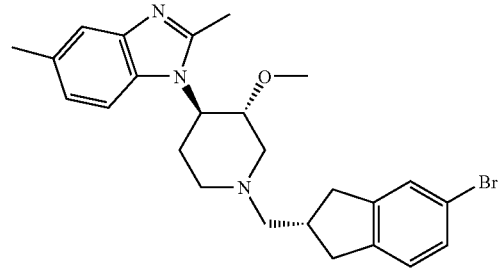

To a flask equipped with a magnetic stir bar and addition funnel under argon atmosphere was added (S)-5-bromo-indan-2-carboxylic acid (383 mg, 1.59 mmol, obtained by following the procedures of patent WO96/23760), EDCI (358 mg, 1.87 mmol), HOBT (291 mg, 2.16 mmol) and $CH_2Cl_2$ (3 mL). This solution was stirred at rt for 5 min. To this solution was then added dropwise a solution of (3R,4R)-1-(3-methoxy-piperidin-4-yl)-2,5-dimethyl-1H-benzoimidazole (375 mg, 1.44 mmol) in $CH_2Cl_2$ (2 mL). The reaction was then stirred at rt overnight for 20 hours. The reaction was quenched by the addition of water (10 mL) and extracted three times with $CH_2Cl_2$. The organic extracts were combined and dried over $Na_2SO_4$, filtered and concentrated in vacuo. Flash chromatography (Biotage 12M column, 3% $CH_3OH$ in ethyl acetate plus 1% $NH_4OH$) afforded the desired product which was contaminated with some HOBT. The product foam was then dissolved in $CH_2Cl_2$ and washed with a saturated $NaHCO_3$ solution. The organic was dried over $Na_2SO_4$, filtered and concentrated under reduced pressure to yield ((S)-5-bromo-indan-2-yl)-[(3R,4R)-4-(2,5-dimethyl-benzoimidazol-1-yl)-3-methoxy-piperidin-1-yl]-methanone (579 mg, 83%) as a light yellow foam. HR-ES(+) m/e calcd for $C_{25}H_{28}N_3O_2Br$ (M+H)$^+$ 482.1438, found 482.1436.

$[\alpha]^{83}_D$=−7.3° (c=0.37, $CH_2Cl_2$).

$^1$H NMR (DMSO-d$_6$, 400 MHz): δ 1.88 (m, 2H), 2.15 (m, 1H, CH), 2.38 (s, 3H, $CH_3$), 2.31-3.52 (m, 3H), 2.50 (s, 3H, $CH_3$), 2.59-2.82 (m, 3H), 2.90 (s, 3H, $OCH_3$), 2.93-3.09 (m, 3H), 3.37 (m, 1H, NCH of $NCH_2$), 3.89 (m, 1H, NCH), 4.08

(m, 1H, OCH), 7.00 (brd, 1H), 7.19 (d, 1H), 7.29 (dd, 1H), 7.31 (brs, 1H, aromatic), 7.42 (brs, 1H, aromatic), 7.44 (brd, 1H, aromatic).

A round bottom flask under argon atmosphere containing a suspension of LiAlH4 (119 mg) in THF (8 mL) was cooled to 0° C. in an ice bath. To this suspension was slowly added a solution of ((S)-5-bromo-indan-2-yl)-[(3R,4R)-4-(2,5-dimethyl-benzoimidazol-1-yl)-3-methoxy-piperidin-1-yl]-methanone (119 mg, 0.25 mmol) in THF (3 mL) via syringe. It was then stirred at 0° C. for 30 minutes, heated at 80° C. for 15 minutes and then cooled back down to 0° C. The reaction was then quenched by adding dropwise water (0.11 mL), 15% aqueous solution of NaOH (0.11 mL) and water (0.33 mL). It was then stirred at 25° C. for one hour and then it was diluted with THF (10 mL) and filtered through Celite® to remove the insoluble material. Flash chromatography (Biotage 40S column, 5% CH₃OH in ethyl acetate) afforded a colorless gum (108 mg) which contained two compounds. This material was then purified on preparative HPLC (Impaq C18, 2×10 cm column 5/95 acetonitrile/water plus 0.1% TFA to 90/10 acetonitrile/water plus 0.1% TFA) to yield 1-[(3R,4R)-1-((S)-5-bromo-indan-2-ylmethyl)-3-methoxy-piperidin-4-yl]-2,5-dimethyl-1H-benzoimidazole (42 mg, 37%) (the second peak to elute off the column free based by washing with 1M K₂CO₃ solution and extracting with 3/2 chloroform/ CH₃OH) as a white solid.

HRMS (M+1)—Calculated 468.1645; Found 468.1645.
[α]³⁰_D=−25.0° (c=0.30, CH₃OH)
¹H NMR (DMSO-d₆, 400 MHz): δ 1.88 (m, 2H), 2.15 (m, 1H), 2.38 (s, 3H), 2.31-3.52 (m, 3H), 2.50 (s, 3H), 2.59-2.82 (m, 3H), 2.90 (s, 3H), 2.93-3.09 (m, 3H), 3.37 (m, 1H), 3.89 (m, 1H), 4.08 (m, 1H), 7.00 (brd, 1H), 7.19 (d, 1H), 7.29 (dd, 1H), 7.31 (brs, 1H), 7.42 (brs, 1H), 7.44 (brd, 1H).

Example 2

Cyclopropanecarboxylic acid {(R)-2-[(3R,4R)-3-hydroxy-4-(2-isopropyl-5-methyl-benzoimidazol-1-yl)-piperidin-1-ylmethyl]-indan-5-yl}-amide

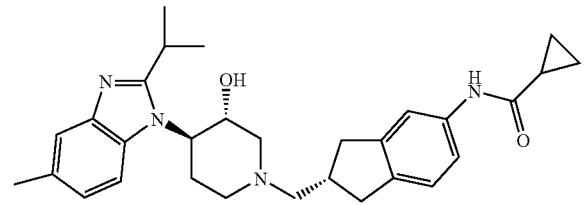

trans-4-(2-isopropyl-5-methyl-benzimidazol-1-yl)-piperidin-3-ol (640 mg; 1.85 mmol was combined with ((R)-2-iodomethyl-indan-5-yl)-carbamic acid tert-butyl ester (690 mg; 1.85 mmol) and Cs₂CO₃ (1.62 g: 4.97 mmol) in 25 mL of acetonitrile and the mixture stirred and heated at 85° C. for 20 hours. An additional 600 mg (1.8 mmol) of cesium carbonate was added and heating and stirring continued for 17 hours. The mixture was cooled, filtered and the filtrate evaporated. The residue was purified by flash chromatography (1-5% CH₃OH in CH₂Cl₂) to give {(R)-2-[3R,4R]-3-Hydroxy-4-(2-isopropyl-5-methyl-benzoimidazol-1-yl)-piperidin-1-ylmethyl}indan-5-yl}-carbamic acid tert-butyl ester (402 mg, 42%) as an amber foam.

The aforementioned foam, {(R)-2-[(3R,4R)-3-Hydroxy-4-(2-isopropyl-5-methyl-benzoimidazol-1-yl)-piperidin-1-ylmethyl]-indan-5-yl}-carbamic acid tert-butyl ester (400 mg, 0.77 mmol), was dissolved in dioxane (4 mL) and 4 mL of 4M anhydrous HCl in dioxane was added to the stirring solution. A few drops of CH₃OH were added to dissolve the tacky solid that came out of solution. Stirring was continued for 90 minutes and the mixture was evaporated to dryness in vacuo. The residue from evaporation was triturated with ethyl ether and the resulting rust colored solid was collected (405 mg) as (3R,4R)-1-((R)-5-amino-indan-2-ylmethyl)-4-(2-isopropyl-5-methyl-benzoimidazol-1-yl)-piperidin-3-ol-trihydrochloride salt.

(3R,4R)-1-((R)-5-amino-indan-2-ylmethyl)-4-(2-isopropyl-5-methyl-benzoimidazool-1-yl)-piperidin-3-ol-trihydrochloride salt (125 mg, 0.237 mmol) was suspended in 2 mL of THF while stirring and triethylamine (170 µL, 1.22 mmol) was added. The mixture was treated with cyclopropanecarbonyl chloride (27 µL, 0.29 mmol) and stirring continued for 2 hours. The mixture was filtered, the filtrate was evaporated and the residue was purified by flash column chromatography (1-5% CH₃OH in CH₂Cl₂) to give cyclopropaneacarboxylic acid {(R)-2-[(3R,4R)-3-hydroxy-4-(2-isopropyl-5-methyl-benzoimidazol-1-yl)-piperidin-1-ylmethyl]-indan-5-yl}-amide.

HRMS (M+1)—Calculated: 487.3068. Found: 487.3064.

Example 3

N-{(R)-2-[4-(2,5-Dimethyl-benzoimidazol-1-yl)-3-hydroxymethyl-piperidin-1-ylmethyl]-indan-5-yl}-isobutyramide

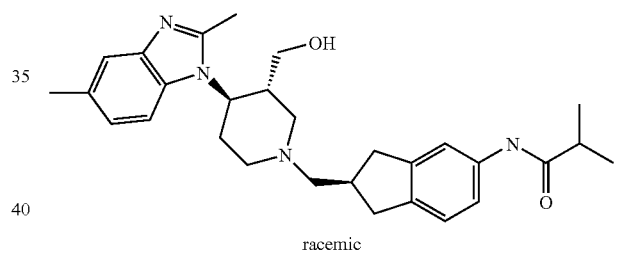

racemic cis-4-(2,5-Dimethylbenzimidazol-1-yl)-3-hydroxymethylpiperidine dihydrochloride (313 mg; 0.94 mmol), 3-[3-iodopropyl]-N-Boc aniline (361 mg. 1 mmol) and Cs₂CO₃ (1625 mg; 5 mmol) were added to CH₃CN (10 mL) and the reaction mixture was heated to reflux for 14 h. After cooling to rt, the reaction mixture was filtered through Celite® and all volatiles were removed under reduced pressure to yield a brown oil from which {2-[4-(2,5-dimethyl-benzoimidazol-1-yl)-3-hydroxymethyl-piperidin-1-ylmethyl]-indan-5-yl}-carbamic acid tert-butyl ester was isolated by flash chromatography (0-10% CH₃OH in EtOAc) as a heavy oil (191 mg; 39%).

{2-[4-(2,5-Dimethyl-benzoimidazol-1-yl)-3-hydroxymethyl-piperidin-1-ylmethyl]-indan-5-yl}-carbamic acid tert-butyl ester (191 mg) was dissolved in 4M HCl in dioxane and stirred for 1 h after which all volatiles were removed under reduced pressure to yield a heavy oil which was suspended in CH₂Cl₂ and washed with 0.1 M NaOH. The organic phase was dried over Na₂CO₃. Filtration and removal of volatiles yielded [1-(5-amino-indan-2-ylmethyl)-4-(2,5-dimethyl-benzoimidazol-1-yl)-piperidin-3-yl]-methanol as a heavy oil (86 mg; 59%)

[1-(5-Amino-indan-2-ylmethyl)-4-(2,5-dimethyl-benzoimidazol-1-yl)-piperidin-3-yl]-methanol (65 mg; 0.165 mmol) was dissolved in CH$_2$Cl$_2$ (1 mL). Diisopropylethylamine (70 µL; 0.4 mmol) and cyclopropanecarbonyl chloride (18 µL; 0.2 mmol) were added and the reaction mixture was stirred for one hour. All volatiles were removed and N-{(R)-2-[4-(2,5-Dimethyl-benzoimidazol-1-yl)-3-hydroxymethyl-piperidin-1-ylmethyl]-indan-5-yl}-isobutyramide was isolated by flash chromatography (1-10% CH$_3$OH in EtOAc) as a waxy oil (68 mg; 90%).

HRMS (M+1)—Calculated: 475.3068. Found: 475.3069.

Example 4

N-{(S)-2-[4-(2-Ethoxy-5-methyl-benzoimidazol-1-yl)-piperidin-1-ylmethyl]-indan-5-yl}-isobutyramide

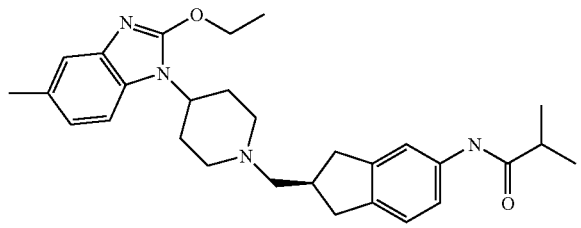

To a 100 mL round bottom flask was added 3-nitro-4-fluorotoluene (1.55 g, 10 mmol), 4-amino-1-N-Boc-piperidine (2.40 g, 12 mmol), powder K$_2$CO$_3$ (2.76 g, 20 mmol) and dry DMF (30 mL). The mixture was stirred at 85° C. overnight. Solvents were evaporated under reduced pressure. The residue was extracted with ethyl acetate and the combined organic layers were washed with brine. The organic layer was dried over Na$_2$SO$_4$ and filtered. Removal of solvents under reduced pressure gave an oil residue. 4-(4-methyl-2-nitrophenylamino)-piperidine-1-carboxylic acid tert-butyl ester was isolated as a solid (3.13 g, 94%) from Biotage flash column chromatography using hexanes and ethyl acetate (3/1 ratio).

4-(4-methyl-2-nitrophenylamino)-piperidine-1-carboxylic acid tert-butyl ester (3.0 g, 8.96 mmol) was dissolved in a mixture of THF and CH$_3$OH (100 mL). Then 10% of Pd on carbon (0.60 g) was added. The mixture was hydrogenated at 50 psi for 2 hrs. The mixture was filtered through a pad of Celite® and washed with CH$_3$OH. The filtrate was evaporated to dryness to give a pink residue as 4-(2-amino-4-methylphenylamino)-piperidine-1-carboxylic acid tert-butyl ester (2.72 g, 100%).

4-(2-Amino-4-methylphenylamino)-piperidine-1-carboxylic acid tert-butyl ester (361 mg, 1.18 mmol) was mixed with tetraethyl carbonate (272 mg, 1.20 eq) in 4 mL of acetic acid. The mixture was stirred at r.t for 4 hrs until all starting material was consumed. The solution was evaporated and the residue was extracted with ethyl acetate and concentrated NaHCO$_3$ solution. The organic layer was dried and solvents were evaporated. The resulting residue was purified on a Biotage flash column chromatography using ethyl acetate and hexanes (1:2 ratio) to give 4-(2-ethoxy-5-methylbenzoimidazol-1-yl)-piperidine-1-carboxylic acid tert-butyl ester (367 mg, 86%) as an oil. ES-MS showed m/e 360 (M$^+$+1). $^1$H-NMR (CDCl$_3$) δ 7.33 (s, 1H), 7.10 (d, 1H), 6.92 (d, 1H), 4.58 (q, 2H), 4.23-4.33 (m, 3H), 2.83 (t, 2H), 2.41 (s, 3H), 2.25-2.31 (m, 2H), 1.82 (d, 2H), 1.49 (s, 9H), 1.46 (t, 3H).

4-(2-ethoxy-5-methylbenzoimidazol-1-yl)-piperidine-1-carboxylic acid tert-butyl ester (367 mg, 1.02 mmol) was dissolved in CH$_2$Cl$_2$ (2 mL) and TFA (1 mL) and the solution was stirred at rt for 1 hour. The mixture was evaporated to dryness and the residue was extracted with CH$_2$Cl$_2$, brine and 2N NaOH solution. The organic layer was washed with brine and dried over Na$_2$SO$_4$. After the evaporation of solvents, an oily residue was obtained (217 mg, 0.84 mmol) as 4-(2-ethoxy-5-methylbenzoimidazol-1-yl)-piperidine which was then was mixed with (S)-(2-iodomethyl-indan-5-yl)-carbamic acid tert-butyl ester (224 mg, 0.60 mmol) and cesium carbonate (817 mg, 2.51 mmol) in acetonitrile (10 mL). The mixture was stirred at 85° C. for 16 hrs. The reaction mixture was filtered and solvents were evaporated. The residue was purified through a Biotage flash column chromatography using 5% CH$_3$OH in CH$_2$Cl$_2$ to give a brownish fluffy material (206 mg, 68%) as (S)-{2-[4-(2-ethoxy-5-methylbenzoimidazol-1-yl)-piperidin-1-ylmethyl]-indan-5-yl}-carbamic acid tert-butyl ester.

(S)-{2-[4-(2-Ethoxy-5-methylbenzoimidazol-1-yl)-piperidin-1-ylmethyl]-indan-5-yl}-carbamic acid tert-butyl ester (206 mg, 0.41 mmol) was dissolved in CH$_2$Cl$_2$ (1 mL) and TFA (1 mL) and the mixture was stirred at r.t for 2 hrs. Solvents were evaporated. The residue was dried under vacuum overnight to give a dark brown residue as an amine triflate salt. This salt was dissolved in CH$_2$Cl$_2$ (5 mL) and triethyl amine (0.36 mL, 6.0 eq). After stirring for 5 minutes, a clear solution was obtained. The mixture was cooled in an ice bath and isobutyryl chloride (0.051 mL, 0.49 mmol) was added. The resulting solution was stirred at 0° C. for 30 min and at r.t for 2 hrs. Solvents were evaporated and residue was extracted with ethyl acetate and water. The organic layer was washed with concentrated NaHCO$_3$ solution and dried over Na$_2$SO$_4$. After the evaporation of solvents, the residue was purified through a Biotage flash column chromatography using 5% of CH$_3$OH in CH$_2$Cl$_2$ to give N-{(S)-2-[4-(2-ethoxy-5-methyl-benzoimidazol-1-yl)-piperidin-1-ylmethyl]-indan-5-yl}-isobutyramide (100 mg, 52%).

$^1$H-NMR (CDCl$_3$) δ 7.52 (s, 1H), 7.33 (s, 1H), 7.24 (d, 1H), 7.13 (m, 3H), 6.94 (d, 1H), 4.59 (q, 2H), 4.16 (br m, 1H), 3.05 (br s, 4H), 2.74 (m, 3H), 2.45 (m, 4H), 2.41 (s, 3H), 2.13 (m, 2H), 1.80 (br d, 2H), 1.48 (t, 3H), 1.24 (d, 6H).

HRMS (M+1)—Calculated: 475.3068; Found 475.3069.

Example 5

N-{(S)-2-[(3R,4R)-4-(2,5-Dimethyl-benzoimidazol-1-yl)-3-hydroxy-piperidin-1-ylmethyl]-indan-5-yl}-propionamide

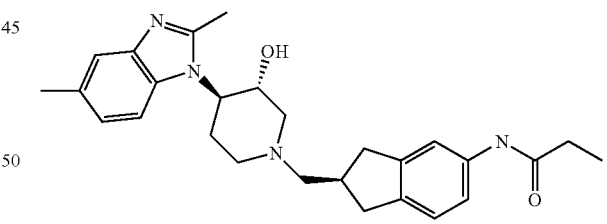

(3R,4R)-1-(S)-(5-amino-indan-2-ylmethyl)-4-(2,5-dimethyl-benzoimidazol-1-yl)-piperidin-3-ol trihydrochloride salt (95 mg, 0.19 mmol, prepared before) was suspended in THF (2 mL) with magnetic stirring. Triethylamine (130 µL, 0.93 mmol) was added and the mixture was stirred while propionyl chloride (21 µL, 0.24 mmol) was added. The mixture was stirred under argon for 2 hours then filtered through a pad of Celite® and evaporated in vacuo. The residue was purified by flash column chromatography eluting with mixtures of CH$_3$OH and CH$_2$Cl$_2$ to provide N-{(S)-2-[(3R,4R)-4-(2,5-dimethyl-benzoimidazol-1-yl)-3-hydroxy-piperidin-1-ylmethyl]indan-5-yl}-propionamide as white foam (27 mg, 32%).

HRMS (M+1)—Calculated: 447.2755. Found: 447.2757.

Example 6

((R)-2-{4-[2-(1-Hydroxy-1-methyl-ethyl)-5-methyl-benzoimidazol-1-yl]-piperidin-1-ylmethyl}-indan-5-yl)-carbamic acid methyl ester

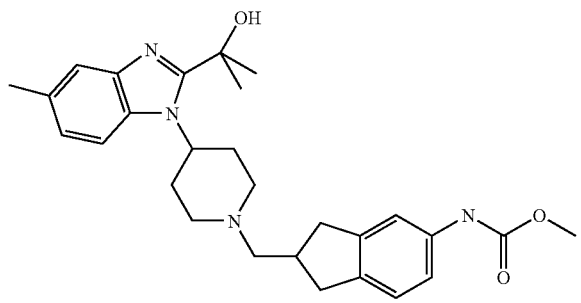

To a solution of 2-(5-methyl-1-piperidin-4-yl-1H-benzoimidazol-2-yl)-propan-2-ol hydrochloride salt (158 mg, 0.55 mmol) in DMF (5 ml) was added N,N-diisopropylethylamine (150 mg, 1.15 mmol). After stirring for 10 minutes, 5-tert-butoxycarbonylamino-indan-2-carboxylic acid (140 mg, 0.55 mmol) was added to the reaction mixture followed by EDCI (195 mg, 1.10 mmol) and HOBT (137 mg, 1.10 mmol). After stirring at rt for 4 hours, the reaction mixture was diluted with water, and the aqueous layer was extracted with ethyl acetate. The combined organic extracts were washed with saturated $NaHCO_3$, brine, and dried over $Na_2SO_4$. The extracts were filtered and concentrated in vacuo to afford (2-{4-[2-(1-hydroxy-1-methyl-ethyl)-5-methyl-benzoimidazol-1-yl]-piperidine-1-carbonyl}-indan-5-yl)-carbamic acid tert-butyl ester (266 mg, 98%) as a white solid without further purification.

LRMS (M+1)—Calculated: 533.3. Found: 533.2.

To a solution of (2-{4-[2-(1-hydroxy-1-methyl-ethyl)-5-methyl-benzoimidazol-1-yl]-piperidine-1-carbonyl}-indan-5-yl)-carbamic acid tert-butyl ester (266 mg, 0.49 mmol) in dioxane (2 mL) was added 4 M HCl (2 ml). After the addition was complete, the reaction mixture was stirred for 1 hour. The solvent mixture was quenched with saturated $NaHCO_3$ and extracted with ethyl acetate, the extracts was dried over $Na_2SO_4$ and concentrated to afford (5-amino-indan-2-yl)-{4-[2-(1-hydroxy-1-methyl-ethyl)-5-methyl-benzoimidazol-1-yl]-piperidin-1-yl}-methanone (200 mg 95%) as a white solid.

LRMS (M+1)—Calculated: 433.2. Found: 433.2.

To a solution of (5-amino-indan-2-yl)-{4-[2-(1-hydroxy-1-methyl-ethyl)-5-methyl-benzoimidazol-1-yl]-piperidin-1-yl}-methanone (150 mg, 0.35 mmol) in THF (10 mL) was added dropwise of 1 M lithium aluminum hydride (0.76 ml, 0.76 mmol) in THF. After stirring for 30 minutes, the reaction mixture was heated up to 80° C. and stirred for 20 minutes. The reaction mixture was quenched with water (0.3 ml) and 4 M NaOH solution (0.1 ml) at 0° C. The mixture was warmed up to rt and stirred for 45 minutes. The suspension was filtered over a Celite® pad, washed with ethyl acetate, and the filtrate was concentrated in vacuo. The residue was purified by flash chromatography to afford 2-{1-[1-(5-amino-indan-2-ylmethyl)-piperidin-4-yl]-5-methyl-1H-benzoimidazol-2-yl}-propan-2-ol (87 mg, 60%) as a white solid.

LRMS (M+1)—Calculated: 419.3. Found: 419.2.

To a solution of 2-{1-[1-(5-amino-indan-2-ylmethyl)-piperidin-4-yl]-5-methyl-1H-benzoimidazol-2-yl}-propan-2-ol (36 mg, 0.096 mmol), N,N-diisopropylethylamine (37 mg, 0.29 mmol) in THF (3 mL) was added methyl chloroformate (9 mg, 0.11 mmol). After stirring overnight, the reaction mixture was quenched with silica-supported diamine-3 (95 mg, Silicycle) to scavenge the excessive amount of methyl chloroformate. The mixture was filtered and concentrated in vacuo, and the residue was purified by flash chromatography eluent to afford (2-{4-[2-(1-hydroxy-1-methyl-ethyl)-5-methyl-benzoimidazol-1-yl]-piperidin-1-ylmethyl}-indan-5-yl)-carbamic acid methyl ester (20 mg, 59%) as white solid.

LRMS (M+1)—Calculated: 477.3. Found: 477.2.

Example 7

Methanesulfonic acid 4-(2,5-dimethyl-benzoimidazol-1-yl)-1-((R)-5-isobutyrylamino-indan-2-ylmethyl)-piperidin-3-yl ester

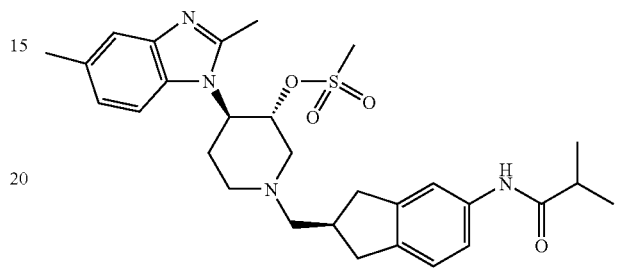

A solution of N-{(S)-2-[(3R,4R)-4-(2,5-Dimethyl-benzoimidazol-1-yl)-3-hydroxy-piperidin-1-ylmethyl]-indan-5-yl}-isobutyramide; compound with trifluoro-acetic acid (235 mg; 0.51 mmol) and diisopropylethylamine (122 mL; 0.7 mmol) in $CH_2Cl_2$ was treated with methanesulfonyl chloride (47 mL; 0.6 mmol). The reaction mixture was stirred for 1 h and then poured into saturated $NaHCO_3$. The aqueous phase was extracted three times with $CH_2Cl_2$ and the combined organic layers were dried over $Na_2SO_4$. Filtration and removal of volatiles under reduced pressure gave a brown solid from which the methanesulfonic acid 4-(2,5-dimethyl-benzoimidazol-1-yl)-1-((R)-5-isobutyrylamino-indan-2-ylmethyl)-piperidin-3-yl ester was isolated by flash chromatography (0-10% $CH_3OH$ in EtOAc) as a waxy solid (171 mg; 62%)

HRMS(M+1)—Calculated: 539.2687. Found: 539.2668.

Example 8

N-((R)-2-{4-[2-(1-Hydroxy-1-methyl-ethyl)-5-methyl-benzoimidazol-1-yl]-piperidin-1-ylmethyl}-indan-5-yl)-propionamide

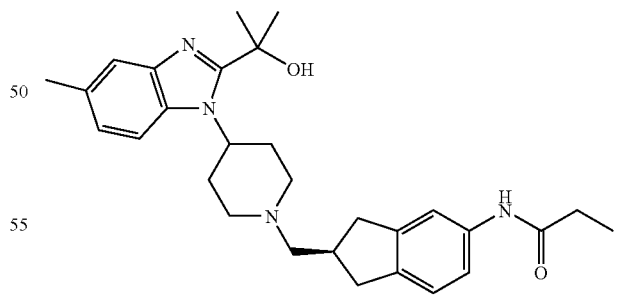

To a solution of 2-{1-[1-(5-amino-indan-2-ylmethyl)-piperidin-4-yl]-5-methyl-1H-benzoimidazol-2-yl}-propan-2-ol (50 mg, 0.12 mmol), N,N-diisopropylethylamine (46 mg, 0.36 mmol) in THF (3 mL) was added propionyl chloride (12 mg, 0.13 mmol). After stirring overnight, the reaction mixture was quenched with silica-supported diamine-3 (119 mg, Silicycle) to scavenge the excess propionyl chloride. The mixture was filtered and concentrated in vacuo, and the residue was purified by flash chromatography to afford N-(2-{4-[2-(1- hydroxy-1-methyl-ethyl)-5-methyl-benzoimidazol-1-yl]-piperidin-1-ylmethyl}-indan-5-yl)-propionamide (54 mg, 95%) as white solid.

LRMS (M+1)—Calculated: 475.3. Found: 475.1.

Example 9

N-{(S)-2-[(3R,4R)-4-(2,5-Dimethyl-benzoimidazol-1-yl)-3-hydroxy-piperidin-1-ylmethyl]-indan-5-yl}-isobutyramide; trifluoroacetic acid salt

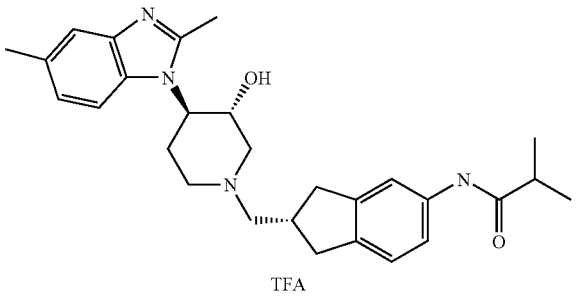

TFA (3R,4R)-1-(S)-(5-amino-indan-2-ylmethyl)-4-(2,5-dimethylbenzoimidazol-1-yl)-piperidin-3-ol trihydrochloride salt was suspended in THF (2 mL) with stirring. Triethylamine (155 μL, 1.1 mmol) was added and the mixture was stirred for 15 minutes. Isobutyryl chloride (28 μL, 0.267 mmol) was added and the mixture stirred for 90 minutes. The reaction mixture was purified by flash column chromatography (1-5% $CH_3OH$/EtOAc) and then through a reverse phase preparative HPLC ($H_2O$/$CH_3CN$ with 0.1% TFA) to give N-{(S)-2-[(3R,4R)-4-(2,5-dimethyl-benzoimidazol-1-yl)-3-hydroxy-piperidin-1-ylmethyl]-indan-5-yl}-isobutyramide; trifluoroacetic acid salt (18.3 mg, 12%).

LRMS (M+1)—Calculated: 461.2. Found: 461.3.

Example 10

N-{(R)-2-[4-(2,6-Dimethyl-imidazo[4,5-c]pyridin-3-yl)-piperidin-1-ylmethyl]-indan-5-yl}-isobutyramide; compound with trifluoro-acetic acid

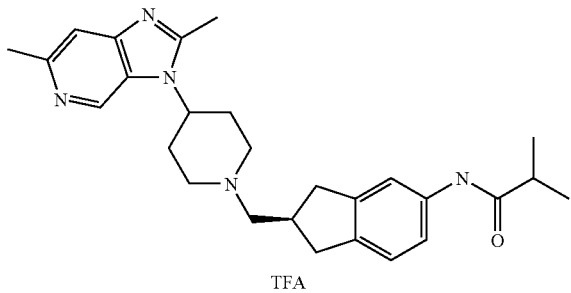

TFA

A solution of 5-bromo-2-methyl-pyridine (1.47 g, 8.54 mmol) in $CH_2Cl_2$ (5 mL) was treated with a cold solution of 30% aqueous hydrogen peroxide (4.6 mL) in acetic acid (13.8 mL) at 0° C. The reaction mixture was then stirred at 50° C. for 18 h and poured into ice water (5 mL). The resulting mixture was adjusted to pH=9 by addition of $K_2CO_3$. The mixture was stirred at rt for 15 min and diluted with $CH_2Cl_2$ (10 mL). The aqueous layer was extracted three tomes with $CH_2Cl_2$. The combined extracts were washed with brine, dried over anhydrous $Na_2SO_4$, filtered and concentrated in vacuo to afford 5-bromo-2-methyl-pyridine N-oxide as a white solid (1.6 g, 99%) which was used without further purification.

A solution of 5-bromo-2-methyl-pyridine N-oxide (536 mg, 2.85 mmol) in concentrated sulfuric acid (3.0 mL) was added dropwise a solution of fuming nitric acid (2.4 mL) in concentrated sulfuric acid (3.2 mL) at 0° C. The reaction mixture was heated at 90° C. for 1.5 h. The reaction mixture was cooled to rt and poured into ice (50 g). The mixture was extracted with $CH_2Cl_2$ (3×20 mL). The combined extracts were washed with a saturated aqueous sodium chloride solution (1×20 mL), dried over anhydrous $Na_2SO_4$, filtered and concentrated in vacuo to afford 5-bromo-2-methyl-4-nitro-pyridine N-oxide as a yellow solid (520 mg, 78%) which was used without further purification 5-Bromo-2-methyl-4-nitro-pyridine N-oxide (520 mg, 2.23 mmol) was mixed with 4-amino-piperidine-1-carboxylic acid tert-butyl ester (1.56 g, 7.80 mmol) in a microwave tube. The reaction mixture was irradiated in a microwave oven at 140° C. for 1 h. The mixture was dissolved in $CH_2Cl_2$ (5 mL). Flash chromatography (10% $CH_3OH$ in $CH_2Cl_2$) afforded 4-(6-methyl-4-nitro-pyridin-N-oxide-3-ylamino)-piperidine-1-carboxylic acid tert-butyl ester (380 mg, 48%) as a red solid.

A solution of 4-(6-methyl-4-nitro-pyridin-N-oxide-3-ylamino)-piperidine-1-carboxylic acid tert-butyl ester (40 mg, 0.113 mmol) in acetic acid (1 mL) was treated with iron powder (80 mg). The reaction mixture was stirred at 115° C. for 5 h and then was treated with acetic anhydride (2 mL). The resulting mixture was heated at 140° C. for 18 h. The solvent was evaporated and the mixture was diluted with water (10 mL). The mixture was adjusted to pH=10 by addition of solid sodium hydroxide. The aqueous mixture was extracted three times with $CH_2Cl_2$. The combined extracts were washed with brine, dried over anhydrous $Na_2SO_4$, filtered and concentrated in vacuo. Flash chromatography (10% $CH_3OH$ in $CH_2Cl_2$) afforded 1-[4-(2,6-dimethyl-imidazo[4,5-c]pyridin-3-yl)-piperidin-1-yl]-ethanone (20 mg, 65%) as a brown solid.

A solution of 1-[4-(2,6-dimethyl-imidazo[4,5-c]pyridin-3-yl)-piperidin-1-yl]-ethanone 20 mg, 0.0735 mmol) in ethanol (0.5 mL) was treated with concentrated HCl (0.5 mL). The reaction mixture was heated at 100° C. for 18 h. The solvent was evaporated and the mixture was diluted with water (2 mL). The mixture was washed with diethyl ether and the aqueous phase was adjusted to pH=10 by addition of a solution of 25% aqueous NaOH. The aqueous mixture was extracted with $CH_2Cl_2$ (5×10 mL). The combined extracts were washed with brine, dried over anhydrous $Na_2SO_4$, filtered and concentrated in vacuo to afford 2,6-dimethyl-3-piperidin-4-yl-3H-imidazo[4,5-c]pyridine (13 mg, 77%) as a light yellow solid which was used without further purification.

$^1$H-NMR (300 MHz, $CDCl_3$): δ=8.85 (s, 1H), 7.41 (s, 1H), 4.25 (m, 1H), 3.34 (d, 2H), 2.82 (t, 2H, 2.65 (s, 3H), 2.35 (m, 2H), 1.93 (d, 2H.

A solution of 2,6-dimethyl-3-piperidin-4-yl-3H-imidazo[4,5-c]pyridine (20 mg, 0.086 mmol) in acetonitrile (0.80 mL) was treated with (R)-(2-iodomethyl-indan-5-yl)-carbamic acid tert-butyl ester (50 mg, 0.13 mmol) and cesium carbonate (85 mg, 0.26 mmol). The mixture was stirred at 85° C. for 4 hrs. The mixture was filtered and the solvent was evaporated. Flash chromatography (10/1 $CH_2Cl_2$/$CH_3OH$) afforded (R)-{2-[4-(2,6-dimethyl-imidazo[4,5-c]pyridin-3-yl)-piperidin-1-ylmethyl]-indan-5-yl}-carbamic acid tert-butyl ester (22 mg, 54%) as a light yellow solid.

(R)-{2-[4-(2,6-Dimethyl-imidazo[4,5-c]pyridin-3-yl)-piperidin-1-ylmethyl]-indan-5-yl}-carbamic acid tert-butyl ester (22 mg, 0.046 mmol) was treated with 4.0 M HCl in dioxane (1.0 mL, 4 mmol). The mixture was stirred at r.t. for 18 hrs. The solvent was evaporated and the residue was dissolved in pyridine (1 mL). The mixture was cooled in an ice bath and was treated with isobutyryl chloride (0.1 mL, 0.96 mmol). The mixture was stirred at rt for 18 hrs. The solvent was evaporated and the crude product was purified on an HPLC column to afford N-{(R)-2-[4-(2,6-dimethyl-imidazo[4,5-c]pyridin-3-yl)-piperidin-1-ylmethyl]-indan-5-yl}-isobutyramide; compound with trifluoroacetic acid (20 mg, 67%) as a light brown oil.

HRMS (M+1)—Calculated: 446.2915. Found: 446.2915.

Example 11

2-{1-[(3R,4R)-1-((S)-5-Bromo-indan-2-ylmethyl)-3-methoxy-piperidin-4-yl]-5-methyl-1H-benzoimidazol-2-yl}-propan-2-ol

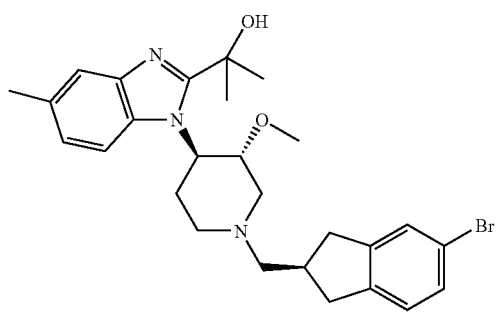

The chiral amine (2R,3'R)-2-[1-(3-methoxy-piperidine-4-yl)-5-methyl-1H-benzimidazol-2-yl]-propanol (1.30 g, 4.29 mmol) was dissolved in 100 mL of dichloroethane at r.t. Sodium triacetoxyborohydride (2.86 g, 3.0 eq) was added. The mixture was stirred at r.t for 20 minutes to give a near clear solution. To this solution was added (S)-5-bromoindan-2-carboxaldehyde (1.0 g, 4.44 mmol) in 7 mL dichloroethane dropwise. The addition was completed in 20 minutes. The mixture was stirred at rt over night and then extracted with CH$_2$Cl$_2$. The combined organic layers were washed with concentrated NaHCO$_3$ solution. The combined organic phase was first washed with 0.1 sodium hydroxide solution and then brine. The organic layer was dried over Na$_2$SO$_4$ and solvents were evaporated. The residue was purified through a flash column chromatography using ethyl acetate and hexane (2:1 ratio) to give 2-{1-[3R,4R]-1-((S)-5-bromo-indan-2-ylmethyl)-3-methoxy-piperidin-4-yl]-5-methyl-1H-benzoimidazol-2-yl}-propan-2-ol as a white solid (1.50 g, 69%).

LRMS (M+1)—Calculated: 513.5. Found: 513.5.

Example 12

2-{1-[1-(6,7-Dihydro-5H-[2]pyridin-6-ylmethyl)-piperidin-4-yl]-5-methyl-1H-benzoimidazol-2-yl}-propan-2-ol

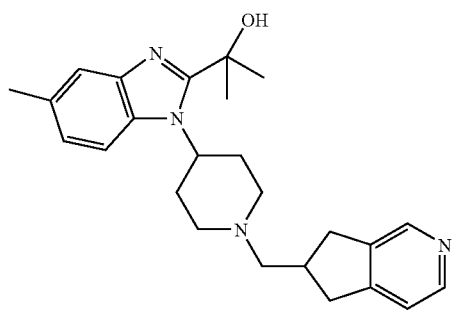

6,7-Dihydro-5H-[2]pyridin-6-carbaldehyde

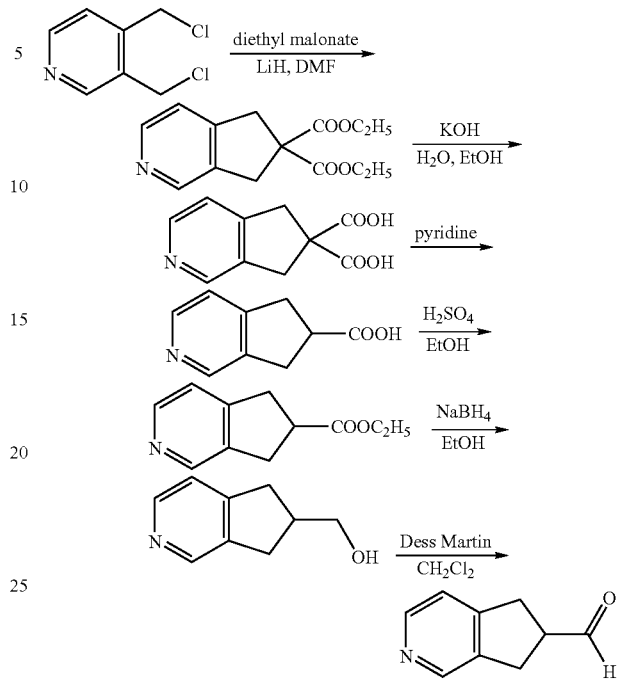

3,4-Bis-chloromethyl-pyridine was prepared from pyridine-3,4-dicarboxylic acid (Aldrich) according to the procedure described by Yoshiizumi et. al. *Bioorganic & Medicinal Chem* 2003, 11 (3), 433-450. The isolated yield of the product after two steps is 76% as oil.

To a solution of diethyl malonate (140 mg, 0.874 mmol) in DMF (2 mL) was added lithium hydride (18 mg, 2.19 mmol) at 0° C. After the evolution of hydrogen gas ceased 3,4-bis-chloromethyl-pyridine (154 mg, 0.874 mmol) was added and the reaction was allowed to warm to rt. After heating for 2 hours at 100° C., the reaction mixture was diluted with water and extracted with ethyl acetate. The combined organic extracts were washed with brine and dried over Na$_2$SO$_4$. The filtrate was concentrated in vacuo and the residue was purified by flash chromatography (30% CH$_3$OH in CH$_2$Cl$_2$) to afford 5,7-dihydro-[2]pyridine-6,6-dicarboxylic acid diethyl ester (159 mg, 76%) as an oil.

A mixture of 5,7-dihydro-[2]pyridine-6,6-dicarboxylic acid diethyl ester (55 mg, 0.209 mmol), KOH (94 mg, 1.67 mmol), H$_2$O (1.5 mL) and ethanol (1.5 mL) was heated to reflux for 24 hours. The reaction mixture was then cooled and the solvent was removed under reduced pressure. The residue was diluted with water and the pH was adjusted to 3-4 with 2 M HCl. The suspension was filtered and the residue was washed with CH$_3$OH. The volatiles were removed under reduced pressure to afford a crude product 5,7-dihydro-[2]pyridine-6,6-dicarboxylic acid (43 mg, 100%) as a yellow solid.

5,7-Dihydro-[2]pyridine-6,6-dicarboxylic acid (40 mg, 0.193 mmol) in pyridine (2 mL) was heated to reflux for 2 h. The solvent was removed under reduced pressure to afford crude product 6,7-dihydro-5H-[2]pyridine-6-carboxylic acid (31 mg, 100%) as a yellow solid.

To a solution of 6,7-dihydro-5H-[2]pyridine-6-carboxylic acid (45 mg, 0.276 mmol) in ethanol (4 mL) was added H$_2$SO$_4$ (0.1 mL) at 0° C. The reaction was allowed to warm to rt and then heated to reflux for 3 h. The reaction mixture was then cooled and all volatiles were removed under reduced pressure. The reaction mixture was adjusted to pH=8 with saturated aqueous NaHCO₃ and the aqueous layer was extracted with ethyl acetate. The combined organic extracts were washed with saturated NaHCO₃, brine, and dried over Na₂SO₄. Filtration followed by removal of volatiles under reduced pressure yielded 6,7-dihydro-5H-[2]pyridine-6-carboxylic acid ethyl ester (45 mg, 76%) as an oil.

To a solution of 6,7-dihydro-5H-[2]pyridine-6-carboxylic acid ethyl ester (40 mg, 0.209 mmol) in ethanol (2 mL) was added NaBH₄ (40 mg, 1.04 mmol) in one portion at 0° C. The reaction mixture was stirred for 5 min at rt and then heated to reflux for 6 hours. The reaction mixture was cooled to rt, filtered, and washed with ethanol. After removal of volatiles under reduced pressure, the residue was purified by flash chromatography (5-10% CH₃OH in CH₂Cl₂) to afford (6,7-dihydro-5H-[2]pyridine-6-yl)methanol (20 mg, 64%) as an oil.

To a solution of (6,7-dihydro-5H-[2]pyridine-6-yl)methanol (20 mg, 0.134 mmol) in CH₂Cl₂ was added Dess-Martin periodinane (80 mg, 0.188 mmol) at 0° C. The reaction was allowed to warm up to rt and stirred for 1 hour. The reaction mixture was diluted with CH₂Cl₂, washed with saturated NaHCO₃, and dried over Na₂SO₄. The extracts were filtered through a pad of silica gel, and concentrated to afford 6,7-dihydro-5H-[2]pyridine-6-carbaldehyde (14 mg, 71%) as an oil.

LRMS (M+1)—Calculated: 405.2. Found: 405.2.

Example 13

2-{6-Fluoro-1-[1-(5-fluoro-indan-2-ylmethyl)-piperidin-4-yl]-5-methyl-1H-benzoimidazol-2-yl}-propan-2-ol

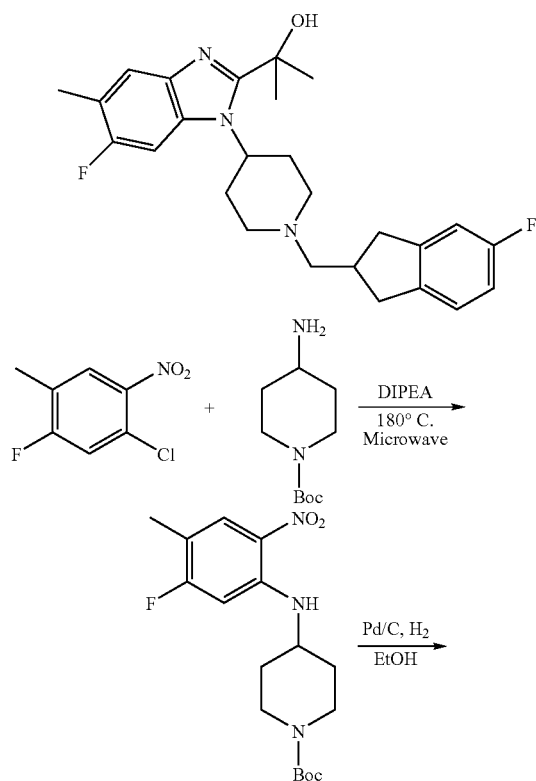

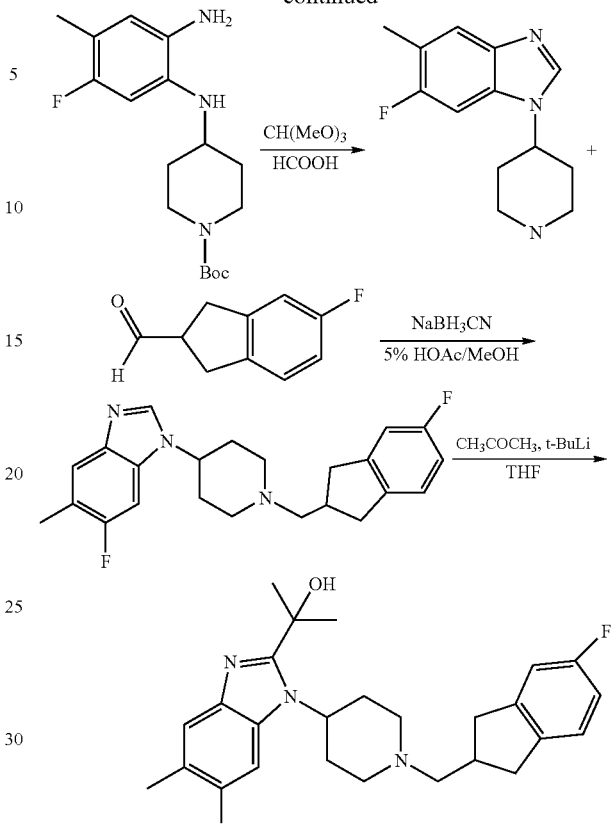

A mixture of 1-chloro-5-fluoro-4-methyl-2-nitro-benzene (2 g, 10.55 mmol), 4-amino-piperidine-1-carboxylic acid tert-butyl ester (2.32 g, 11.58 mmol), and ⁱPr₂NEt (3.8 mL) was heated for 2 hours at 180° C. by microwave heating. After cooling, the reaction mixture was diluted with CH₂Cl₂ and then filtered. The volatiles were removed under reduced pressure and the residue was purified by flash chromatography (25% ethyl acetate in hexanes) to afford 4-(5-fluoro-4-methyl-2-nitro-phenylamino)piperidine-1-carboxylic acid tert-butyl ester (0.68 g, 18%) as a brown solid.

A solution of 4-(5-fluoro-4-methyl-2-nitro-phenylamino)-piperidine-1-carboxylic acid tert-butyl ester (680 mg, 1.92 mmol) and 10% Pd/C (68 mg) in ethanol (20 mL) was shaken under hydrogen (50 psi) for 4 hours. The reaction mixture was filtered through a pad of Celite® and the volatiles were removed. The residue was purified by flash chromatography (10% CH₃OH in CH₂Cl₂) to afford 4-(2-amino-5-fluoro-4-methyl-phenylamino)piperidine-1-carboxylic acid tert-butyl ester (500 mg, 80%) as an oil.

To a solution of 4-(2-amino-5-fluoro-4-methyl-phenylamino)piperidine-1-carboxylic acid tert-butyl ester (250 mg, 0.309 mmol) in formic acid (3 mL) was added methyl orthoformate (0.5 mL). After heating for 3 hours at 60° C., the volatiles was removed under reduced pressure to afford crude product 6-fluoro-5-methyl-1-piperidin-4-yl-1H-benzoimidazole (180 mg, 99%) as a brown solid.

A mixture of 6-fluoro-5-methyl-1-piperidin-4-yl-1H-benzoimidazole (70 mg, 0.300 mmol) and 5-fluoroindane-2-carbaldehyde (49 mg, 0.300 mmol) in CH₃OH (4 mL) and acetic acid (0.2 mL) was stirred at rt for 15 minutes. NaCNBH₃ (40 mg, 0.635 mmol) was added and then the reaction mixture was stirred for 1 hour. The solvent was removed and the residue was diluted with CH₂Cl₂. The organic layers were washed with saturated NaHCO₃, brine, and dried over Na₂SO₄. The organic extracts were removed under the reduced pressure and the residue was purified by flash chromatography (5% CH₃OH in CH₂Cl₂) to afford 6-fluoro-1-[1-(5-fluoro-indan-2-ylmethyl)-piperidin-4-yl]-5-methyl-1H-benzoimidazole (28 mg, 24%) as a white solid.

To a solution of 6-fluoro-1-[1-(5-fluoro-indan-2-ylmethyl)-piperidin-4-yl]-5-methyl-1H-benzoimidazole (25 mg, 0.065 mmol) in anhydrous THF (2 mL) was added tert-BuLi (0.058 mL, 1.7 M in pentane) at −78° C. After stirring for 10 minutes, anhydrous acetone (0.008 mL) was added and the reaction mixture was stirred at −78° C. for 40 minutes. After quenching with 1 M HCl (0.2 mL) the mixture was allowed to warm to rt. The solvent was removed under reduced pressure and the residue was diluted with ethyl acetate. The organic layers were washed with saturated NaHCO₃, brine, and dried over Na₂SO₄. The extracts were removed and the residue was purified by flash chromatography (20/1 CH₂Cl₂/CH₃OH) to afford 2-{6-fluoro-1-[1-(5-fluoro-indan-2-ylmethyl)-piperidin-4-yl]-5-methyl-1H-benzoimidazol-2-yl}-propan-2-ol (5 mg, 17%) as a white solid.

LRMS (M+1)—Calculated: 440.2. Found: 440.2.

Table 1 below presents in vitro activity data, coupling method and masses of representative compounds of the invention. In vitro activity (binding assay) is indicated by the following: +++=IC₅₀<20 nM; ++=20 nM<IC₅₀<200 nM; +=200 nM<IC₅₀<5000 Nm.

TABLE 1

| Example | Systematic Name | IC₅₀ (nM) | Coupling Method | Calcd M + 1 | Found |
|---|---|---|---|---|---|
| 1 | 1-[(3R,4R)-1-((S)-5-Bromo-indan-2-ylmethyl)-3-methoxy-piperidin-4-yl]-2,5-dimethyl-1H-benzoimidazole | +++ | A | 468.1645 | 468.1645 |
| 2 | Cyclopropanecarboxylic acid {(R)-2-[(3R,4R)-3-hydroxy-4-(2-isopropyl-5-methyl-benzoimidazol-1-yl)-piperidin-1-ylmethyl]-indan-5-yl}-amide | ++ | B | 487.3068 | 487.3064 |
| 3 | N-{(R)-2-[4-(2,5-Dimethyl-benzoimidazol-1-yl)-3-hydroxymethyl-piperidin-1-ylmethyl]-indan-5-yl}-isobutyramide | +++ | B | 475.3068 | 475.3069 |
| 4 | N-{(S)-2-[4-(2-Ethoxy-5-methyl-benzoimidazol-1-yl)-piperidin-1-ylmethyl]-indan-5-yl}-isobutyramide | ++ | B | 475.3068 | 475.3069 |
| 5 | N-{(S)-2-[(3R,4R)-4-(2,5-Dimethyl-benzoimidazol-1-yl)-3-hydroxy-piperidin-1-ylmethyl]-indan-5-yl}-propionamide | ++ | B | 447.2755 | 447.2757 |
| 6 | ((R)-2-{4-[2-(1-Hydroxy-1-methyl-ethyl)-5-methyl-benzoimidazol-1-yl]-piperidin-1-ylmethyl}-indan-5-yl)-carbamic acid methyl ester | ++ | B | 477.3 | 477.2 |
| 7 | Methanesulfonic acid 4-(2,5-dimethyl-benzoimidazol-1-yl)-1-((R)-5-isobutyrylamino-indan-2-ylmethyl)-piperidin-3-yl ester; dihydrochloride | ++ | B | 539.2687 | 539.2668 |
| 8 | N-((R)-2-{4-[2-(1-Hydroxy-1-methyl-ethyl)-5-methyl-benzoimidazol-1-yl]-piperidin-1-ylmethyl}-indan-5-yl)-propionamide | ++ | B | 475.3 | 475.1 |
| 9 | N-{(S)-2-[(3R,4R)-4-(2,5-Dimethyl-benzoimidazol-1-yl)-3-hydroxy-piperidin-1-ylmethyl]-indan-5-yl}-isobutyramide; compound with trifluoroacetic acid | ++ | B | 461.2000 | 461.3 |
| 10 | N-{(R)-2-[4-(2,6-Dimethyl-imidazo[4,5-c]pyridin-3-yl)-piperidin-1-ylmethyl]-indan-5-yl}-isobutyramide; compound with trifluoroacetic acid | + | B | 446.2915 | 446.2915 |

TABLE 1-continued

| Example | Systematic Name | IC$_{50}$ (nM) | Coupling Method | Calcd M + 1 | Found |
|---|---|---|---|---|---|
| 11 | 2-{1-[(3R,4R)-1-((S)-5-Bromo-indan-2-ylmethyl)-3-methoxy-piperidin-4-yl]-5-methyl-1H-benzoimidazol-2-yl}-propan-2-ol | +++ | C | 513.5 | 513.5 |
| 12 | 2-{1-[1-(6,7-Dihydro-5H-[2]pyrindin-6-ylmethyl)-piperidin-4-yl]-5-methyl-1H-benzoimidazol-2-yl}-propan-2-ol | ++ | C | 405.2 | 405.2 |
| 13 | 2-{6-Fluoro-1-[1-(5-fluoro-indan-2-ylmethyl)-piperidin-4-yl]-5-methyl-1H-benzoimidazol-2-yl}-propan-2-ol | +++ | C | 440.2 | 440.2 |
| 14 | 2-{1-[1-(5-Chloro-indan-2-ylmethyl)-piperidin-4-yl]-5-methyl-1H-benzoimidazol-2-yl}-propan-2-ol | +++ | A or C | 438.2307 | 438.2309 |
| 15 | N-{(R)-2-[(3S,4S)-4-(2,5-Dimethyl-benzoimidazol-1-yl)-3-(2-hydroxy-2-methyl-propoxy)-piperidin-1-ylmethyl]-indan-5-yl}-isobutyramide; dihydrochloride | +++ | B | 533.3486 | 533.3483 |
| 16 | N-{(R)-2-[(3R,4R)-4-(2,5-Dimethyl-benzoimidazol-1-yl)-3-methoxy-piperidin-1-ylmethyl]-indan-5-yl}-isobutyramide; dihydrochloride | ++ | B | 475.3068 | 475.3063 |
| 17 | 1-[(3S,4S)-1-((S)-5-Bromo-indan-2-ylmethyl)-3-methoxy-piperidin-4-yl]-2-isopropyl-5-methyl-1H-benzoimidazole | ++ | B | 496.1958 | 496.1960 |
| 18 | 1-[(3R,4R)-1-((S)-5-Bromo-indan-2-ylmethyl)-3-methoxy-piperidin-4-yl]-2-isopropyl-5-methyl-1H-benzoimidazole | ++ | B | 496.1958 | 496.1955 |
| 19 | 1-[(3S,4S)-1-(5-Chloro-indan-2-ylmethyl)-3-methoxy-piperidin-4-yl]-2,5-dimethyl-1H-benzoimidazole; dihydrochloride | ++ | A | 424.2150 | 424.2150 |
| 20 | 1-[(3R,4R)-1-(5-Fluoro-indan-2-ylmethyl)-3-methoxy-piperidin-4-yl]-2,5-dimethyl-1H-benzoimidazole | ++ | A | 408.2446 | 408.2447 |
| 21 | N-{(R)-2-[(3R,4R)-4-(2,5-Dimethyl-benzoimidazol-1-yl)-3-(2-hydroxy-2-methyl-propoxy)-piperidin-1-ylmethyl]-indan-5-yl}-isobutyramide; dihydrochloride | ++ | B | 533.3486 | 533.3482 |
| 22 | N-{(R)-2-[4-(2,5-Dimethyl-benzoimidazol-1-yl)-3-methylsulfanyl-piperidin-1-ylmethyl]-indan-5-yl}-isobutyramide; dihydrochloride | ++ | B | 491.2839 | 491.2839 |
| 23 | 1-{1-[1-(5-Fluoro-indan-2-ylmethyl)-piperidin-4-yl]-5-methyl-1H-benzoimidazol-2-yl}-2-methyl-propan-2-ol; dihydrochloride | ++ | A | 436.2759 | 436.2760 |

TABLE 1-continued

| Example | Systematic Name | IC$_{50}$ (nM) | Coupling Method | Calcd M + 1 | Found |
|---------|-----------------|----------------|-----------------|-------------|-------|
| 24 | 1-((3R,4R)-1-Indan-2-ylmethyl-3-methoxy-piperidin-4-yl)-2-isopropyl-5-methyl-1H-benzoimidazole | ++ | A | 418.2853 | 418.2854 |
| 25 | N-{(R)-2-[(3R,4R)-4-(5-Fluoro-2-methyl-benzoimidazol-1-yl)-3-methoxy-piperidin-1-ylmethyl]-indan-5-yl}-propionamide; dihydrochloride | ++ | B | 465.2661 | 465.2660 |
| 26 | 1-[(3R,4R)-1-((S)-5-Bromo-indan-2-ylmethyl)-3-methoxy-piperidin-4-yl]-2-tert-butyl-5-methyl-1H-benzoimidazole | ++ | A | 509.2 | 509.1 |
| 27 | N-{(R)-2-[4-(2,5-Dimethyl-benzoimidazol-1-yl)-3-hydroxy-piperidin-1-ylmethyl]-indan-5-yl}-isobutyramide; dihydrochloride | + | B | 461.2911 | 461.2912 |
| 28 | Cyclopropanecarboxylic acid {(R)-2-[(3R,4R)-4-(5-fluoro-2-methyl-benzoimidazol-1-yl)-3-methoxy-piperidin-1-ylmethyl]-indan-5-yl}-amide; dihydrochloride | + | B | 477.2661 | 477.2660 |
| 29 | 1-((3S,4S)-1-Indan-2-ylmethyl-3-methoxy-piperidin-4-yl)-2-isopropyl-5-methyl-1H-benzoimidazole | + | A | 418.2853 | 418.2854 |
| 30 | Cyclopropanecarboxylic acid {(R)-2-[4-(2-chloro-5-methyl-benzoimidazol-1-yl)-piperidin-1-ylmethyl]-indan-5-yl}-amide; dihydrochloride | + | B | 463.2259 | 463.2262 |
| 31 | (R)-2-[4-(2-Chloro-5-methyl-benzoimidazol-1-yl)-piperidin-1-ylmethyl]-indan-5-ylamine; dihydrochloride | + | B | 395.1997 | 395.1997 |
| 32 | N-{(R)-2-[(3S,4S)-4-(2-Isopropyl-5-methyl-benzoimidazol-1-yl)-3-methoxy-piperidin-1-ylmethyl]-indan-5-yl}-propionamide | +++ | A | 489.3224 | 489.3223 |
| 33 | N-{(R)-2-[4-(5-Methyl-2-phenyl-benzoimidazol-1-yl)-piperidin-1-ylmethyl]-indan-5-yl}-isobutyramide | +++ | A | 507.3119 | 507.312 |
| 34 | N-{(R)-2-[(3S,4S)-4-(2,5-Dimethyl-benzoimidazol-1-yl)-3-methoxy-piperidin-1-ylmethyl]-indan-5-yl}-isobutyramide | +++ | B | 475.3068 | 475.3062 |
| 35 | N-{(R)-2-[4-(2,5-Dimethyl-benzoimidazol-1-yl)-piperidin-1-ylmethyl]-indan-5-yl}-isobutyramide | +++ | B | 445.2962 | 445.2958 |
| 36 | N-{(R)-2-[4-(2,5-Dimethyl-benzoimidazol-1-yl)-3-hydroxymethyl-piperidin-1-ylmethyl]-indan-5-yl}-isobutyramide | +++ | B | 475.3068 | 475.3067 |
| 37 | N-{(R)-2-[4-(5-Methyl-2-phenyl-benzoimidazol-1-yl)-piperidin-1-ylmethyl]-indan-5-yl}-isobutyramide dihydrochloride | +++ | A | 507.3118 | 507.3117 |

TABLE 1-continued

| Example | Systematic Name | IC$_{50}$ (nM) | Coupling Method | Calcd M + 1 | Found |
|---|---|---|---|---|---|
| 38 | N-{(S)-2-[4-(2,5-Dimethyl-benzoimidazol-1-yl)-piperidin-1-ylmethyl]-indan-5-yl}-2-thiophen-2-yl-acetamide | +++ | C | 499.2526 | 499.2529 |
| 39 | N-{(S)-2-[(3R,4R)-4-(2,5-Dimethyl-benzoimidazol-1-yl)-3-methoxy-piperidin-1-ylmethyl]-indan-5-yl}-isobutyramide; dihydrochloride | +++ | B | 475.3068 | 475.3066 |
| 40 | {(R)-2-[4-(2-tert-Butyl-5-methyl-benzoimidazol-1-yl)-piperidin-1-ylmethyl]-indan-5-yl}-carbamic acid methyl ester | +++ | A | 475.3068 | 475.307 |
| 41 | N-{(R)-2-[4-(2-tert-Butyl-5-methyl-benzoimidazol-1-yl)-piperidin-1-ylmethyl]-indan-5-yl}-isobutyramide | +++ | A | 487.3432 | 487.3433 |
| 42 | {(R)-2-[4-(5-Methyl-2-phenyl-benzoimidazol-1-yl)-piperidin-1-ylmethyl]-indan-5-yl}-carbamic acid methyl ester | +++ | A | 495.2755 | 495.2754 |
| 43 | N-{(S)-2-[(3R,4R)-4-(2,5-Dimethyl-benzoimidazol-1-yl)-3-methoxy-piperidin-1-ylmethyl]-indan-5-yl}-isobutyramide | ++ | B | 475.3068 | 475.3067 |
| 44 | -{(S)-2-[4-(2,5-Dimethyl-benzoimidazol-1-yl)-piperidin-1-ylmethyl]-indan-5-yl}-butyramide | ++ | C | 445.2962 | 445.2965 |
| 45 | N-{(R)-2-[(3R,4R)-4-(2-Isopropyl-5-methyl-benzoimidazol-1-yl)-3-methoxy-piperidin-1-ylmethyl]-indan-5-yl}-propionamide | ++ | A | 489.3224 | 489.3222 |
| 46 | N-{2-[4-(2,5-Dimethyl-benzoimidazol-1-yl)-piperidin-1-ylmethyl]-indan-5-yl}-isobutyramide | ++ | C | 445.2962 | 445.2956 |
| 47 | N-{(R)-2-[(3R,4R)-4-(2,5-Dimethyl-benzoimidazol-1-yl)-3-methoxy-piperidin-1-ylmethyl]-indan-5-yl}-isobutyramide | ++ | A or B | 475.3068 | 475.3065 |
| 48 | N-{(S)-2-[4-(2,5-Dimethyl-benzoimidazol-1-yl)-piperidin-1-ylmethyl]-indan-5-yl}-isobutyramide | ++ | B | 445.2962 | 445.2958 |
| 49 | N-{(S)-2-[(3S,4S)-4-(2,5-Dimethyl-benzoimidazol-1-yl)-3-methoxy-piperidin-1-ylmethyl]-indan-5-yl}-isobutyramide | ++ | B | 475.3068 | 475.3064 |
| 50 | 1-((3R,4R)-1-Indan-2-ylmethyl-3-methoxy-piperidin-4-yl)-2,5-dimethyl-1H-benzoimidazole | ++ | A | 390.2540 | 390.2541 |
| 51 | N-{2-[4-(2,5-Dimethyl-benzoimidazol-1-yl)-piperidin-1-ylmethyl]-indan-5-yl}-2-methyl-butyramide | ++ | C | 459.3119 | 459.3122 |
| 52 | (R)-2-[4-(5-Methyl-2-phenyl-benzoimidazol-1-yl)-piperidin-1-ylmethyl]-indan-5-ylamine | ++ | A | 437.2700 | 437.2702 |
| 53 | N-{2-[4-(2,5-Dimethyl-benzoimidazol-1-yl)-piperidin-1-ylmethyl]-3H-inden-5-yl}-isobutyramide | ++ | A | 443.2806 | 443.2805 |

TABLE 1-continued

| Example | Systematic Name | IC$_{50}$ (nM) | Coupling Method | Calcd M + 1 | Found |
|---|---|---|---|---|---|
| 54 | N-{2-[4-(2,5-Dimethyl-benzoimidazol-1-yl)-piperidin-1-ylmethyl]-1H-inden-5-yl}-isobutyramide | + | A | 443.2806 | 443.2805 |
| 55 | 1-((3R,4R)-1-Indan-2-ylmethyl-3-methoxy-piperidin-4-yl)-2,5-dimethyl-1H-benzoimidazole; dihydrochloride | + | A | 431.3169 | 431.3168 |
| 56 | {(R)-2-[4-(2-tert-Butyl-5-methyl-benzoimidazol-1-yl)-piperidin-1-ylmethyl]-indan-5-yl}-methyl-amine | + | A | 415.2380 | 415.2382 |
| 57 | N-{(R)-2-[(3R,4R)-4-(2,5-Dimethyl-benzoimidazol-1-yl)-3-methoxy-piperidine-1-carbonyl]-indan-5-yl}-isobutyramide | + | D | 459.3119 | 459.3118 |
| 58 | N-(2-{2-[4-(2,5-Dimethyl-benzoimidazol-1-yl)-piperidin-1-yl]-ethyl}-indan-5-yl)-isobutyramide | + | B | 447.2755 | 447.2755 |
| 59 | N-{(R)-2-[4-(2-Isopropyl-5-methyl-benzoimidazol-1-yl)-3-methoxy-piperidin-1-ylmethyl]-indan-5-yl}-propionamide | +++ | B | 489.3 | 489.3 |
| 60 | N-{(R)-2-[(3S,4S)-4-(2-Cyclopropyl-5-methyl-benzoimidazol-1-yl)-3-methoxy-piperidin-1-ylmethyl]-indan-5-yl}-propionamide | +++ | B | 487.3 | 487.4 |
| 61 | N-{(R)-2-[4-(2-Ethyl-5-methyl-benzoimidazol-1-yl)-3-methoxy-piperidin-1-ylmethyl]-indan-5-yl}-isobutyramide | +++ | B | 489.3 | 489.3 |
| 62 | N-{(R)-2-[(3S,4S)-4-(2-Cyclopropyl-5-methyl-benzoimidazol-1-yl)-3-methoxy-piperidin-1-ylmethyl]-indan-5-yl}-butyramide | +++ | B | 501.3 | 501.3 |
| 63 | N-{(R)-2-[(3S,4S)-4-(2-Cyclopropyl-5-methyl-benzoimidazol-1-yl)-3-methoxy-piperidin-1-ylmethyl]-indan-5-yl}-2,2-difluoro-acetamide | +++ | B | 509.3 | 509.2 |
| 64 | Cyclopropanecarboxylic acid {(R)-2-[4-(2-isopropyl-5-methyl-benzoimidazol-1-yl)-3-methoxy-piperidin-1-ylmethyl]-indan-5-yl}-amide | +++ | B | 501.3 | 501.2 |
| 65 | N-{(R)-2-[(3S,4S)-4-(2-Cyclopropyl-5-methyl-benzoimidazol-1-yl)-3-methoxy-piperidin-1-ylmethyl]-indan-5-yl}-isobutyramide | +++ | B | 501.3 | 501.4 |
| 66 | Cyclopropanecarboxylic acid {(R)-2-[(3S,4S)-4-(2-cyclopropyl-5-methyl-benzoimidazol-1-yl)-3-methoxy-piperidin-1-ylmethyl]-indan-5-yl}-amide | +++ | B | 499.3 | 499.3 |

TABLE 1-continued

| Example | Systematic Name | IC$_{50}$ (nM) | Coupling Method | Calcd M + 1 | Found |
|---|---|---|---|---|---|
| 67 | 2,2-Difluoro-N-{(R)-2-[(3S,4S)-4-(2-isopropyl-5-methyl-benzoimidazol-1-yl)-3-methoxy-piperidin-1-ylmethyl]-indan-5-yl}-acetamide | +++ | B | 511.3 | 511.2 |
| 68 | N-{(R)-2-[4-(2-Isopropyl-5-methyl-benzoimidazol-1-yl)-3-methoxy-piperidin-1-ylmethyl]-indan-5-yl}-isobutyramide | +++ | B | 503.3 | 503.4 |
| 69 | N-{(R)-2-[4-(2-Ethyl-5-methyl-benzoimidazol-1-yl)-3-methoxy-piperidin-1-ylmethyl]-indan-5-yl}-propionamide | +++ | B | 475.3 | 475.2 |
| 70 | N-{2-[4-(2-Ethyl-5-methyl-benzoimidazol-1-yl)-piperidin-1-ylmethyl]-indan-5-yl}-isobutyramide | +++ | C | 459.3 | 459.8 |
| 71 | {(R)-2-[(3S,4S)-4-(2-Cyclopropyl-5-methyl-benzoimidazol-1-yl)-3-methoxy-piperidin-1-ylmethyl]-indan-5-yl}-carbamic acid methyl ester | +++ | B | 489.3 | 489.3 |
| 72 | Cyclopropanecarboxylic acid {(R)-2-[4-(2-ethyl-5-methyl-benzoimidazol-1-yl)-3-methoxy-piperidin-1-ylmethyl]-indan-5-yl}-amide | ++ | B | 487.3 | 487.3 |
| 73 | N-{(R)-2-[(3R,4R)-4-(2-Cyclopropyl-5-methyl-benzoimidazol-1-yl)-3-methoxy-piperidin-1-ylmethyl]-indan-5-yl}-isobutyramide | ++ | B | 501.3 | 501.3 |
| 74 | Cyclopropanecarboxylic acid {2-[4-(2-ethyl-5-methyl-benzoimidazol-1-yl)-piperidin-1-ylmethyl]-indan-5-yl}-amide | ++ | C | 457.3 | 457.2 |
| 75 | {(R)-2-[(3R,4R)-4-(2-Cyclopropyl-5-methyl-benzoimidazol-1-yl)-3-methoxy-piperidin-1-ylmethyl]-indan-5-yl}-carbamic acid methyl ester | ++ | B | 489.3 | 489.3 |
| 76 | N-{(R)-2-[(3R,4R)-4-(2-Cyclopropyl-5-methyl-benzoimidazol-1-yl)-3-methoxy-piperidin-1-ylmethyl]-indan-5-yl}-propionamide | ++ | B | 487.3 | 487.3 |
| 77 | {(R)-2-[(3R,4R)-4-(2-Isopropyl-5-methyl-benzoimidazol-1-yl)-3-methoxy-piperidin-1-ylmethyl]-indan-5-yl}-carbamic acid methyl ester | ++ | A | 491.3 | 491.2 |
| 78 | N-{2-[4-(5-Methyl-benzoimidazol-1-yl)-piperidin-1-ylmethyl]-indan-5-yl}-isobutyramide | ++ | C | 431.3 | 431.1 |
| 79 | N-{(R)-2-[(3R,4R)-4-(2-Cyclopropyl-5-methyl-benzoimidazol-1-yl)-3-methoxy-piperidin-1-ylmethyl]-indan-5-yl}-butyramide | ++ | B | 501.3 | 501.3 |

TABLE 1-continued

| Example | Systematic Name | IC$_{50}$ (nM) | Coupling Method | Calcd M + 1 | Found |
|---|---|---|---|---|---|
| 80 | Cyclopropanecarboxylic acid {(R)-2-[(3R,4R)-4-(2-cyclopropyl-5-methyl-benzoimidazol-1-yl)-3-methoxy-piperidin-1-ylmethyl]-indan-5-yl}-amide | + | B | 499.3 | 499.3 |
| 81 | 1-((3S,4S)-1-Indan-2-ylmethyl-3-methoxy-piperidin-4-yl)-2,5-dimethyl-1H-benzoimidazole | + | B | 390.2540 | 390.2539 |
| 82 | 1-[1-(1-Indan-2-ylmethyl-piperidin-4-yl)-5-methyl-1H-benzoimidazol-2-yl]-ethanone | + | B | 388.2384 | 388.2384 |
| 83 | (3R,4R)-1-Indan-2-ylmethyl-4-(2-isopropyl-5-methyl-benzoimidazol-1-yl)-piperidin-3-ol | + | A | 404.2697 | 404.2698 |
| 84 | N-{(R)-2-[(3R,4R)-3-Hydroxy-4-(2-isopropyl-5-methyl-benzoimidazol-1-yl)-piperidin-1-ylmethyl]-indan-5-yl}-propionamide | +++ | B | 475.3068 | 475.3069 |
| 85 | (S)-2-[(3R,4R)-4-(2,5-Dimethyl-benzoimidazol-1-yl)-3-methoxy-piperidin-1-ylmethyl]-indan-5-carbonitrile | +++ | C | 415.2493 | 415.2493 |
| 86 | N-{(R)-2-[(3R,4R)-3-Hydroxy-4-(2-isopropyl-5-methyl-benzoimidazol-1-yl)-piperidin-1-ylmethyl]-indan-5-yl}-isobutyramide | ++ | B | 489.3224 | 489.3223 |
| 87 | 1-[(3R,4R)-1-((R)-5-Bromo-indan-2-ylmethyl)-3-methoxy-piperidin-4-yl]-2,5-dimethyl-1H-benzoimidazole; dihydrochloride | ++ | A | 469.4400 | 469.11 |
| 88 | Cyclopropanecarboxylic acid {(S)-2-[(3R,4R)-4-(2,5-dimethyl-benzoimidazol-1-yl)-3-hydroxy-piperidin-1-ylmethyl]-indan-5-yl}-amide | ++ | B | 459.2755 | 459.2753 |
| 89 | 1-[(3R,4R)-1-((R)-5-Bromo-indan-2-ylmethyl)-3-methoxy-piperidin-4-yl]-2-isopropyl-5-methyl-1H-benzoimidazole | ++ | B | 496.1958 | 496.196 |
| 90 | 1-[(3S,4S)-1-((R)-5-Bromo-indan-2-ylmethyl)-3-methoxy-piperidin-4-yl]-2-isopropyl-5-methyl-1H-benzoimidazole | + | B | 496.1958 | 496.1959 |
| 91 | 1-[(3S,4S)-1-((S)-5-Bromo-indan-2-ylmethyl)-3-methoxy-piperidin-4-yl]-2,5-dimethyl-1H-benzoimidazole; dihydrochloride | ++ | A | 468.1645 | 468.1644 |
| 92 | 1-[(3S,4S)-3-Methoxy-1-(5-methoxy-indan-2-ylmethyl)-piperidin-4-yl]-2,5-dimethyl-1H-benzoimidazole; dihydrochloride | ++ | A | 420.2646 | 420.2644 |
| 93 | 2-Isopropyl-1-[(3S,4S)-3-methoxy-1-(5-methoxy-indan-2-ylmethyl)-piperidin-4-yl]-5-methyl-1H-benzoimidazole dihydrochloride | ++ | A | 448.2959 | 448.2959 |

TABLE 1-continued

| Example | Systematic Name | IC$_{50}$ (nM) | Coupling Method | Calcd M + 1 | Found |
|---|---|---|---|---|---|
| 94 | 1-[(3S,4S)-1-(5,6-Dichloro-indan-2-ylmethyl)-3-methoxy-piperidin-4-yl]-2,5-dimethyl-1H-benzoimidazole; dihydrochloride | + | A | 458.1761 | 458.176 |
| 95 | 1-[(3S,4S)-1-(5,6-Dichloro-indan-2-ylmethyl)-3-methoxy-piperidin-4-yl]-2-isopropyl-5-methyl-1H-benzoimidazole; dihydrochloride | + | A | 486.2074 | 486.2074 |
| 96 | 2-{1-[1-((R)-5-Bromo-indan-2-ylmethyl)-piperidin-4-yl]-5-methyl-1H-benzoimidazol-2-yl}-propan-2-ol | ++ | C | 482.1802 | 482.1801 |
| 97 | 1-[(3R,4R)-1-(4-Chloro-indan-2-ylmethyl)-3-methoxy-piperidin-4-yl]-2,5-dimethyl-1H-benzoimidazole | ++ | B | 424.2150 | 424.215 |
| 98 | 2-Isopropyl-1-[(3R,4R)-1-(5-isopropyl-indan-2-ylmethyl)-3-methoxy-piperidin-4-yl]-5-methyl-1H-benzoimidazole | + | B | 460.7 | 460.7 |
| 99 | 2-{1-[1-((S)-5-Bromo-indan-2-ylmethyl)-piperidin-4-yl]-5-methyl-1H-benzoimidazol-2-yl}-propan-2-ol | +++ | C | 482.1802 | 482.1803 |
| 100 | 1-[(3S,4S)-1-(5,6-Difluoro-indan-2-ylmethyl)-3-methoxy-piperidin-4-yl]-2-isopropyl-5-methyl-1H-benzoimidazole | ++ | B | 454.2665 | 454.2666 |
| 101 | 1-[(3S,4S)-1-(5,6-Difluoro-indan-2-ylmethyl)-3-methoxy-piperidin-4-yl]-2,5-dimethyl-1H-benzoimidazole | ++ | B | 426.2352 | 426.2353 |
| 102 | 1-[1-(4-Chloro-indan-2-ylmethyl)-piperidin-4-yl]-5-methyl-1H-benzoimidazole; compound with trifluoroacetic acid | + | A | 380.1888 | 380.1888 |
| 103 | 2-{1-[1-(4-Chloro-indan-2-ylmethyl)-piperidin-4-yl]-5-methyl-1H-benzoimidazol-2-yl}-propan-2-ol; compound with trifluoroacetic acid | ++ | C | 438.2307 | 438.2308 |
| 104 | 1-[(3R,4R)-1-(5-Isopropyl-indan-2-ylmethyl)-3-methoxy-piperidin-4-yl]-2,5-dimethyl-1H-benzoimidazole | + | B | 432.6 | 432.6 |
| 105 | 2-(1-Fluoro-1-methyl-ethyl)-5-methyl-1-[1-(5-methyl-indan-2-ylmethyl)-piperidin-4-yl]-1H-benzoimidazole | + | C | 420.2810 | 420.2809 |
| 106 | 6-Fluoro-1-[1-(5-fluoro-indan-2-ylmethyl)-piperidin-4-yl]-5-methyl-1H-benzoimidazole | ++ | A | 382.0 | 382.1 |
| 107 | 2-[1-((3R,4R)-1-Indan-2-ylmethyl-3-methoxy-piperidin-4-yl)-5-methyl-1H-benzoimidazol-2-yl]-propan-2-ol | ++ | C | 434.2802 | 434.2802 |

TABLE 1-continued

| Example | Systematic Name | IC$_{50}$ (nM) | Coupling Method | Calcd M + 1 | Found |
|---|---|---|---|---|---|
| 108 | 2-{1-[(3R,4R)-1-((S)-5-Fluoro-indan-2-ylmethyl)-3-methoxy-piperidin-4-yl]-5-methyl-1H-benzoimidazol-2-yl}-propan-2-ol | ++ | C | 452.0 | 452.0 |
| 109 | 2-{1-[(3R,4R)-1-((R)-5-Fluoro-indan-2-ylmethyl)-3-methoxy-piperidin-4-yl]-5-methyl-1H-benzoimidazol-2-yl}-propan-2-ol | ++ | C | 452.0 | 452.0 |
| 110 | 2-{5-Fluoro-1-[(3R,4R)-3-methoxy-1-(5-methyl-indan-2-ylmethyl)-piperidin-4-yl]-1H-benzoimidazol-2-yl}-propan-2-ol | ++ | C | 452.2708 | 452.2705 |
| 111 | 2-{1-[(3R,4R)-1-((S)-5-Bromo-indan-2-ylmethyl)-3-methoxy-piperidin-4-yl]-5-fluoro-1H-benzoimidazol-2-yl}-propan-2-ol | ++ | C | 516.1657 | 516.1658 |
| 112 | 2-{1-[(3R,4R)-1-((S)-5-Chloro-indan-2-ylmethyl)-3-methoxy-piperidin-4-yl]-5-methyl-1H-benzoimidazol-2-yl}-propan-2-ol | ++ | C | 469.1 | 469.1 |
| 113 | 2-{1-[(3R,4R)-1-((R)-5-Chloro-indan-2-ylmethyl)-3-methoxy-piperidin-4-yl]-5-methyl-1H-benzoimidazol-2-yl}-propan-2-ol | +++ | C | 469.1 | 469.1 |
| 114 | (3R,4R)-4-[2-(1-Hydroxy-1-methyl-ethyl)-5-methyl-benzoimidazol-1-yl]-1-(5-methyl-indan-2-ylmethyl)-piperidin-3-ol | ++ | C | 434.2802 | 434.2802 |
| 115 | 2-{1-[(3R,4R)-1-((R)-5-Bromo-indan-2-ylmethyl)-3-methoxy-piperidin-4-yl]-5-methyl-1H-benzoimidazol-2-yl}-propan-2-ol | ++ | C | 513.1 | 513.1 |
| 116 | 2-{1-[(3S,4S)-1-((R)-5-Bromo-indan-2-ylmethyl)-3-methoxy-piperidin-4-yl]-5-methyl-1H-benzoimidazol-2-yl}-propan-2-ol | ++ | C | 513.1 | 513.0 |
| 117 | 2-{1-[(3R,4R)-3-Methoxy-1-(5-methyl-indan-2-ylmethyl)-piperidin-4-yl]-5-methyl-1H-benzoimidazol-2-yl}-propan-2-ol | ++ | C | 448.2959 | 448.2959 |
| 118 | 1-[(3R,4R)-1-(5-Fluoro-indan-2-ylmethyl)-3-methoxy-piperidin-4-yl]-5-methyl-1H-benzoimidazole | + | A | 394.5 | 394.5 |
| 119 | 1-[(3R,4R)-1-(6,7-Dihydro-5H-[2]pyrindin-6-ylmethyl)-3-methoxy-piperidin-4-yl]-2,5-dimethyl-1H-benzoimidazole | ++ | C | 391.5 | 391.5 |
| 120 | (S)-2-{(3R,4R)-4-[2-(1-Hydroxy-1-methyl-ethyl)-5-methyl-benzoimidazol-1-yl]-3-methoxy-piperidin-1-ylmethyl}-indan-5-carbonitrile | +++ | C | 459.2755 | 459.2754 |

TABLE 1-continued

| Example | Systematic Name | IC$_{50}$ (nM) | Coupling Method | Calcd M + 1 | Found |
|---|---|---|---|---|---|
| 121 | 1-[1-((S)-5-Bromo-indan-2-ylmethyl)-piperidin-4-yl]-5-methanesulfonyl-2-trifluoromethyl-1H-benzoimidazole | ++ | C | 557.4 | 557.4 |
| 122 | (3R,4R)-1-((S)-5-Bromo-indan-2-ylmethyl)-4-[2-(1-hydroxy-1-methyl-ethyl)-5-methyl-benzoimidazol-1-yl]-piperidin-3-ol | +++ | C | 498.1751 | 498.1750 |
| 123 | 2-{1-[(3R,4R)-1-((S)-5-Bromo-indan-2-ylmethyl)-3-methoxy-piperidin-4-yl]-6-fluoro-5-methyl-1H-benzoimidazol-2-yl}-propan-2-ol | +++ | C | 529.2 | 529.3 |
| 124 | 2-{1-[1-((S)-5-Bromo-indan-2-ylmethyl)-piperidin-4-yl]-6-fluoro-5-methyl-1H-benzoimidazol-2-yl}-propan-2-ol | +++ | C | 501.1 | 501.1 |
| 125 | (3R,4R)-1-((S)-5-Bromo-indan-2-ylmethyl)-4-[2-(1-hydroxy-1-methyl-ethyl)-5-methyl-benzoimidazol-1-yl]-piperidin-3-ol | +++ | C | 497.2 | 497.2 |

Table 2 below presents selected in vitro MCH-R Binding Data:

TABLE 2

| Example | Structure | Systematic Name | IC50 (nM) |
|---|---|---|---|
| 1 | 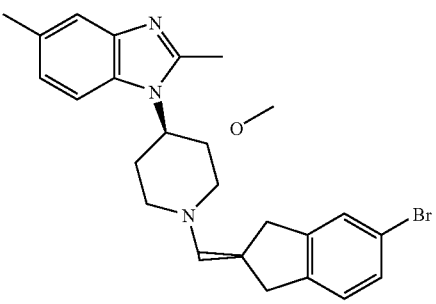 | 1-[(3R,4R)-1-((S)-5-Bromo-indan-2-ylmethyl)-3-methoxy-piperidin-4-yl]-2,5-dimethyl-1H-benzoimidazole | 20 |
| 13 | 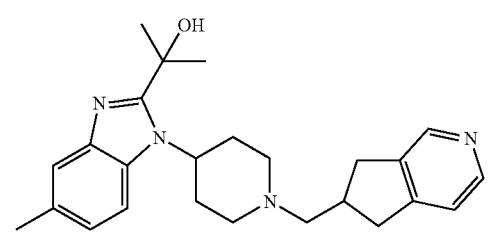 | 2-{1-[1-(6,7-Dihydro-5H-[2]pyrindin-6-ylmethyl)-piperidin-4-yl]-5-methyl-1H-benzoimidazol-2-yl}-propan-2-ol | 106 |

TABLE 2-continued

| Example | Structure | Systematic Name | IC50 (nM) |
|---|---|---|---|
| 33 | 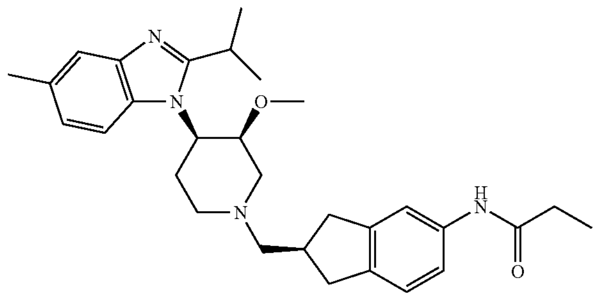 | N-{(R)-2-[(3S,4S)-4-(2-Isopropyl-5-methyl-benzoimidazol-1-yl)-3-methoxy-piperidin-1-ylmethyl]-indan-5-yl}-propionamide | 4 |
| 66 | 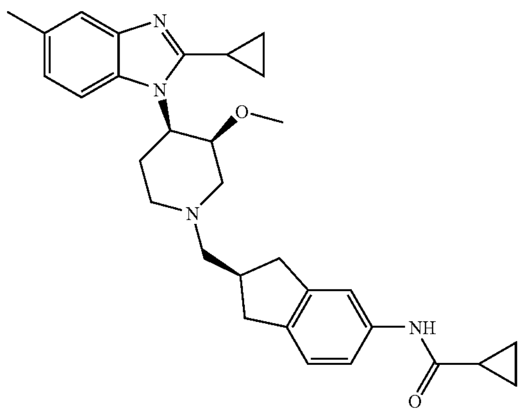 | Cyclopropanecarboxylic acid {(R)-2-[(3S,4S)-4-(2-cyclopropyl-5-methyl-benzoimidazol-1-yl)-3-methoxy-piperidin-1-ylmethyl]-indan-5-yl}-amide | 12 |
| 106 | 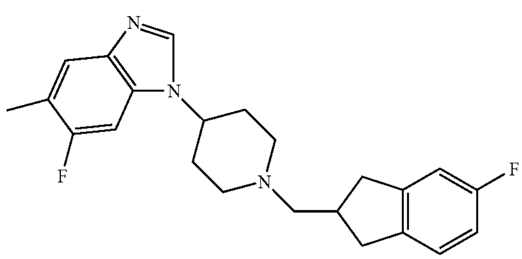 | 6-Fluoro-1-[1-(5-fluoro-indan-2-ylmethyl)-piperidin-4-yl]-5-methyl-1H-benzoimidazole | 194 |
| 121 | 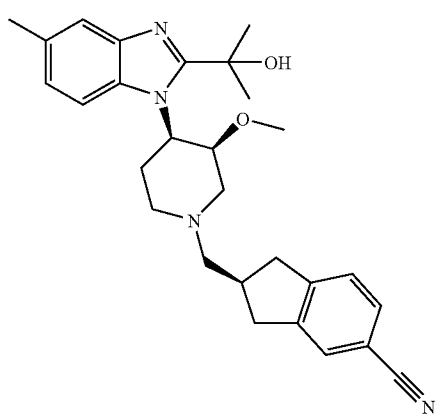 | (S)-2-{(3R,4R)-4-[2-(1-Hydroxy-1-methyl-ethyl)-5-methyl-benzoimidazol-1-yl]-3-methoxy-piperidin-1-ylmethyl}-indan-5-carbonitrile | 5 |

TABLE 2-continued

| Example | Structure | Systematic Name | IC50 (nM) |
|---|---|---|---|
| 122 | (structure) | 1-[1-((S)-5-Bromo-indan-2-ylmethyl)-piperidin-4-yl]-5-methanesulfonyl-2-trifluoromethyl-1H-benzoimidazole | 35 |
| 126 | (structure) | (3R,4R)-1-((S)-5-Bromo-indan-2-ylmethyl)-4-[2-(1-hydroxy-1-methyl-ethyl)-5-methyl-benzoimidazol-1-yl]-piperidin-3-ol | 2 |

Example 127

MCHR Filter Binding Assay

Competition binding assays were performed using membranes from CHO-K1 cells stably expressing the recombinant human MCHR1-receptors. Binding reactions (90 μl, final volume) were carried out at rt by incubating 2.8 μg membranes with 0.2 nM [Phe$^{13}$,[$^{125}$I]Tyr$^{19}$]-MCH (PerkinElmer) in the absence or presence of various concentrations of competing ligands in binding buffer (50 mM HEPES, 2.5 mM CaCl$_2$, 0.05 mM BSA, 1 mM phenanthroline, 0.03 mM Triton X-100). [Phe$^{13}$,[$^{125}$I]Tyr$^{19}$]-MCH was added 15 min following the addition of unlabeled competing ligands, and the reactions incubated for a 1 h period. The reactions were terminated by rapid filtration over pretreated 96-well filter plates (Millipore; MultiScreen 0.65 μm GFB filter plates). Filter Plates were treated for 12 h at 4° C. with a 0.5% polyvinylpyrrolidone solution containing 1% BSA and 0.1% Tween 20, and then washed with an ice-cold solution of 10 mM Tris, pH 7.5 (5×200 μl). The plates were drained following a 5 min incubation with binding buffer (200 μl) at rt. Following termination of the binding reactions, the filters were washed with ice-cold binding buffer (4×200 μl). The filter plates were air dried for 30 min, scintillation cocktail (60 μl) added to each well and radioactivity bound to the plates was determined using a Micro-beta plate reader (Wallace/PerkinElmer).

Example 128

Cyclic AMP Assay

The functional antagonist activities of select compounds of the invention were characterized in CHO-K1 cells stably expressing high levels of human MCH-R1 receptors. The cells were cultured in DMEM/F12 medium containing 10% FBS, 1% Pen/Strep, and 500 mg/ml G418 and grown until they reached 75-85% confluence.

The cells were harvested 18 h prior to assay with 5 ml Versene®, washed with DMEM/F12 medium and then plated into clear 384-well plates (9000 cells/well) containing DMEM/F12 medium without phenol red, 10% FBS, 1% Pen/Strep, and 500 mg/ml G418. Prior to assay, the culture medium was replaced with a DMEM/F12 medium without phenol red (50 μl/well) containing 0.5 mM 3-isobutyl-1-methylxanthine, 0.5 mg/ml BSA, 5 μM forskolin, and 0.4 nM human MCH. The cells were incubated in the dark for 30 min at 25° C. in the absence or presence of varying concentrations of antagonists (1.1 μl, 100% DMSO). The incubation media was discarded and replaced with the assay lysis buffer (50 μl/well) provided in the Tropix kit (Applied Biosystems) and the plates incubated for 45 min at 37° C. The intracellular levels of cAMP generated in the CHO-K1 cells were measured using the Tropix Kit. In brief, 20 μl of the lysate was transferred into pre-coated antibody plates (384-well; Tropix kit) along with 10 μl of alkaline phosphatase conjugate and 20 μl of anti-cAMP antibody and the plates were incubated for 1 h at rt while shaking. The plates were then washed 5 times with wash buffer (70 μl) and tapped dry. CSPD/Sapphire-II RTU substrate/enhancer solution (30 μl) was added and plates incubated for 45 min at rt while shaking. The signal generated was measured using a luminometer. (VICTOR-V; 1 sec/well).

It is to be understood that the invention is not limited to the particular embodiments of the invention described above, as variations of the particular embodiments may be made and still fall within the scope of the appended claims.

What is claimed is:

1. A compound of the formula (I):

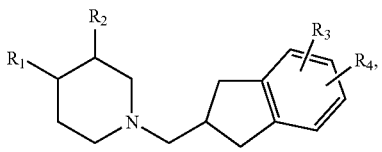

wherein:

R₁ is

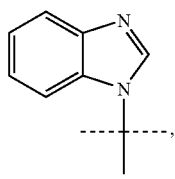

unsubstituted or mono-, di- or tri-substituted with a group selected from the group consisting of halogen, hydroxyl, —SCH₃, phenyl, (C₃-C₆)cycloalkyl, oxygen, (C₁-C₆) alkoxy, branched or unbranched ⁻(C₁-C₆)alkyl and branched or unbranched (C₁-C₆)alkyl substituted with hydroxyl;

R₂ is hydrogen, halogen, substituted or unsubstituted (C₁-C₆)alkyl, hydroxyl, —OCH₂C(CH₃)OH, —SCH₃, —OSO₂CH₃, (C₁-C₆)alkoxy, —CH₂OH or —CH₂OCH₃;

R₃ is H or halogen;

R₄ is hydrogen, halogen, (C₁-C₆)alkyl, —CN, —NH₂, —NHCH₃, —NHCO—R₅, —OCH₃ or azaindane;

R₅ is substituted or unsubstituted, branched or unbranched (C₁-C₆)alkyl, (C₁-C₆)alkoxy, (C₃-C₆)cycloalkyl, or a heterocycle which is a 5- or 6-membered heteroaromatic ring connected by a ring carbon which has from 1 to 3 hetero ring atoms selected from the group consisting of S, N and O;

and pharmaceutically acceptable salts thereof.

2. The compound according to claim 1, wherein R₁ is substituted at positions 2 and 5.

3. The compound according to claim 1, wherein said compound is (S)-2-{(3R,4R)-4-[6-Fluoro-2-(1-hydroxy-1-methyl-ethyl)-5-methyl-benzoimidazol-1-yl]-3 methoxy-piperidin-1-ylmethyl}-indan-5-carbonitrile.

4. The compound according to claim 1, wherein said compound is N—((R)-2-{(3R,4R)-4-[6-Fluoro-2-(1-hydroxy-1-methyl-ethyl)-5-methyl-benzoimidazol-1-yl]-3-methoxy-piperidin-1-ylmethyl}-indan-5-yl)-propionamide.

5. The compound according to claim 1, wherein said compound is (S)-2-{(3S,4S)-4-[2-(1-Hydroxy-1-methyl-ethyl)-5-methyl-benzoimidazol-1-yl]-3-methoxy-piperidin-1-ylmethyl}-indan-5-carbonitrile.

6. The compound according to claim 1, wherein said compound is (3R,4R)-1-((S)-5-Bromo-indan-2-ylmethyl)-4-(2,5-dimethyl-benzoimidazol-1-yl)-piperidin-3-ol.

7. The compound according to claim 1, wherein said compound is (S)-2-[(3R,4R)-3-Methoxy-4-(5-methyl-benzoimidazol-1-yl)-piperidin-1-ylmethyl]-indan-5-carbonitrile.

8. The compound according to claim 1, wherein said compound is 2-[1-((3R,4R)-1-Indan-2-ylmethyl-3-methoxy-piperidin-4-yl)-5-methyl-1H-benzoimidazol-2-yl]-propan-2-ol.

9. The compound according to claim 1, wherein said compound is 2-{1-[(3R,4R)-1-((S)-5-Bromo-indan-2-ylmethyl)-3-methoxy-piperidin-4-yl]-5-methyl-1H-benzoimidazol-2-yl}-propan-2-ol.

10. The compound according to claim 1, wherein said compound is 2-{1-[(3R,4R)-1-(5-Fluoro-indan-2-ylmethyl)-3-methoxy-piperidin-4-yl]-5-methyl-1H-benzoimidazol-2-yl}-propan-2-ol.

11. The compound according to claim 1, wherein said compound is N—((R)-2-{4-[2-(1-Hydroxy-1-methyl-ethyl)-5-methyl-benzoimidazol-1-yl]-piperidin-1-ylmethyl}-indan-5-yl)-propionamide.

12. The compound according to claim 1, wherein said compound is (S)-2-[(3R,4R)-4-(2,5-Dimethyl-benzoimidazol-1-yl)-3-methoxy-piperidin-1-ylmethyl]-indan-5-carbonitrile.

13. A pharmaceutical composition comprising a therapeutically effective amount of a compound according to claim 1 or a pharmaceutically acceptable salt thereof, and a pharmaceutically acceptable carrier.

14. A method for treating obesity, comprising administering a therapeutically effective amount of a compound or a pharmaceutically acceptable salt thereof according to claim 1 to a patient in need thereof.

15. The method according to claim 14 wherein said therapeutically effective amount is from about 0.01 mg/kg to about 50 mg/kg per day.

16. The method according to claim 15, wherein said therapeutically effective amount is from about 0.3 mg/kg to about 10 mg/kg per day.

* * * * *